US006770444B2

(12) United States Patent

Adham et al.

(10) Patent No.: US 6,770,444 B2

(45) Date of Patent: Aug. 3, 2004

(54) METHODS OF IDENTIFYING OR SCREENING FOR AGENTS THAT BINDS THE OB-RE

(75) Inventors: Nika Adham, Ridgewood, NJ (US); Beth Borowsky, Montclair, NJ (US); Nigel Levens, Allschwil (CH); Radek Ctirad Skoda, Basel (CH)

(73) Assignee: Synaptic Pharmaceutical Corporation, Paramus, NJ (US)

(*) Notice: Subject to any disclaimer, the term of this patent is extended or adjusted under 35 U.S.C. 154(b) by 229 days.

(21) Appl. No.: 09/116,676

(22) Filed: Jul. 16, 1998

(65) Prior Publication Data

US 2003/0073829 A1 Apr. 17, 2003

(51) Int. Cl.[7] .......... G01N 33/53

(52) U.S. Cl. .......... 435/7.1; 530/350; 536/23.5; 435/7.21; 435/7.8; 435/325; 435/356; 435/357; 435/361; 435/365; 435/366; 435/369; 435/192.1; 514/12

(58) Field of Search .......... 435/7.1, 7.2, 7.21, 435/7.82, 7.8; 514/2

(56) References Cited

U.S. PATENT DOCUMENTS

| | | | | |
|---|---|---|---|---|
| 5,643,748 | A | 7/1997 | Snodgrass et al. | 435/69.1 |
| 5,763,211 | A | 6/1998 | Snodgrass et al. | 435/69.1 |
| 5,856,098 | A | 1/1999 | Snodgrass et al. | 435/6 |
| 5,869,610 | A | 2/1999 | Snodgrass et al. | 530/350 |
| 5,912,123 | A | 6/1999 | Snodgrass et al. | 435/6 |
| 5,972,621 | A | 10/1999 | Tartaglia et al. | 435/7.1 |
| 6,007,998 | A | 12/1999 | Rosenblum et al. | 435/7.1 |

FOREIGN PATENT DOCUMENTS

| | | |
|---|---|---|
| WO | 9608510 | 3/1996 |
| WO | 9712037 | 4/1997 |
| WO | 9725424 | 7/1997 |
| WO | 9726335 | 7/1997 |
| WO | 9742340 | 11/1997 |

OTHER PUBLICATIONS

Grasso et al. In Vivo Effects of Leptin–Related Synthetic Peptides on Body Weight and Food Intake in Female ob/ob mice. Endocrinology 138(4):1413–1418, Apr. 1997.*

Jackson et al. Human leptin has natriuretic activity in the rat. American Journal of Physiology 272(3):F333–F338, Mar. 1997.*

Verploegen et al. A human leptin mutant induces weight gain in normal mice.FEBS Letts. 405(2):237–240, Mar. 1997.*

Kutoh et al. *Life Sciences* 62(5) 1998, p 445–51.

Rock, et al, *Horm. Metab Res* 28, 1996, p 748–50.

Fong et al, *Mol. Pharmacol* 53, 1998, p 234–40.

Devos et al; *JBC.* 272(29) 1997, p 18304.

Bjorbaek et al *JBC* 272(51) 1997, p 32686.

Murakami et al, *Biochem. Biophys Res Comm* 231, 1997, p 26.

Chung et al, *Diabetes* 46,1997.

Chua et al, *Genomics* 45, 1997, p 264–70.

Wang et al, *FEBS* 392, 1996, p 87–90.

Lollmann et al, *Biochem Biophy Res Comm* 238,1997.

Genbank Accession # AF007819, released Jul. 16, 1997 (Exhibit 2).

Genbank Accession # U59259, released Oct. 3, 1996 (Exhibit 3).

Genbank Accession # AF039456, released Jan. 10, 199 (Exhibit 4).

Genbank Accession # U49110, released Feb. 17, 1996 (Exhibit 5).

DDBJ Accession #D85559, released Sep. 5, 1996 (Exhibit 6).

Genbank Accession # AA028211, released Sep. 12, 1996 (Exhibit 7).

Swissport Accession # O54986, released Jun. 1, 1998 (Exhibit 8).

Swissport Accession # O35773, released Jan. 1, 1998 (Exhibit 9).

Swissport Accession # P70495, released Feb. 1, 1997 (Exhibit 10).

Lee, G., et al., "Abnormal splicing of the leptin receptor in diabetic mice," *Nature* (1996) 379:632–635 (Exhibit 12).

Cioffi, J.A., et al., "Novel B219/OB receptor isoforms: Possible role of letpin in hematopoiesis and reproduction: " *Nature Medicine* (1996) 2: 585–589 (Exhibit 13).

Tartaglia, L.A., et al., "Identification and Expression Cloning of a Leptin Receptor OB–R," *Cell* (1995) 83: 1263–1271 (Exhibit 14).

Liu, C., et al., "Expression and Characterization of a Putative High Affiniity Human Soluble Leptin Receptor," *Endocrinology* (1997) 138: 3548–3554 (Exhibit 16).

* cited by examiner

*Primary Examiner*—Elizabeth Kemmerer
*Assistant Examiner*—Eileen O'Hara
(74) *Attorney, Agent, or Firm*—John P. White; Cooper & Dunham LLP

(57) ABSTRACT

This invention provides an isolated nucleic acid encoding a polypeptide, a purified polypeptide, vectors comprising isolated nucleic acid encoding a polypeptide, cells comprising such vectors, antibodies directed to a polypeptide, nucleic acid probes useful for detecting nucleic acid encoding a polypeptide, antisense oligonucleotides complementary to unique sequences of nucleic acid encoding a polypeptide, nonhuman transgenic animals which express DNA encoding a normal or a mutant polypeptide, methods of isolating a polypeptide, methods of treatment eating disorders as well as methods of determining binding of compounds to polypeptides.

12 Claims, 14 Drawing Sheets

FIG. 3A

Sequence across the mouse intron-exon border:

aatgttaaaaagtttcacatccacggtatgtgtactgtacttttcatggattag

N V K K F H I H G M C T V L F M D *

Sequence across the human intron-exon border:

tctgttaagaagtattatatccatggtaagtttactatactttag

Mouse Ob-Re: ggtatgtgtactgtacttttcatggat
Human Ob-Re: ggtaagtttactatactt

Mouse Ob-Re: G M C T V L F M D
Human Ob-Re: G K F T I L

FIG. 4A

```
1     ATGATTTGTCAAAAATTCTGTGTGGTTTTGTTACATTGGGAATTTATTTATGTGATAACT   60
61    GCGTTTAACTTGTCATATCCAATTACTCCTTGGAGATTTAAGTTGTCTTGCATGCCACCA   120
121   AATTCAACCTATGACTACTTCCTTTTGCCTGCTGGACTCTCAAAGAATACTTCAAATTCG   180
181   AATGGACATTATGAGACAGCTGTTGAACCTAAGTTTAATTCAAGTGGTACTCACTTTTCT   240
241   AACTTATCCAAAACAACTTTCCACTGTTGCTTTCGGAGTGAGCAAGATAGAAACTGCTCC   300
301   TTATGTGCAGACAACATTGAAGGAAAGACATTTGTTTCAACAGTAAATTCTTTAGTTTTT   360
361   CAACAAATAGATGCAAACTGGAACATACAGTGCTGGCTAAAAGGAGACTTAAAATTATTC   420
421   ATCTGTTATGTGGAGTCATTATTTAAGAATCTATTCAGGAATTATAACTATAAGGTCCAT   480
481   CTTTTATATGTTCTGCCTGAAGTGTTAGAAGATTCACCTCTGGTTCCCCAAAAAGGCAGT   540
541   TTTCAGATGGTTCACTGCAATTGCAGTGTTCATGAATGTTGTGAATGTCTTGTGCCTGTG   600
601   CCAACAGCCAAACTCAACGACACTCTCCTTATGTGTTTGAAAATCACATCTGGTGGAGTA   660
661   ATTTTCCAGTCACCTCTAATGTCAGTTCAGCCCATAAATATGGTGAAGCCTGATCCACCA   720
721   TTAGGTTTGCATATGGAAATCACAGATGATGGTAATTTAAAGATTTCTTGGTCCAGCCCA   780
781   CCATTGGTACCATTTCCACTTCAATATCAAGTGAAATATTCAGAGAATTCTACAACAGTT   840
841   ATCAGAGAAGCTGACAAGATTGTCTCAGCTACATCCCTGCTAGTAGACAGTATACTTCCT   900
901   GGGTCTTCGTATGAGGTTCAGGTGAGGGGCAAGAGACTGGATGGCCCAGGAATCTGGAGT   960
961   GACTGGAGTACTCCTCGTGTCTTTACCACACAAGATGTCATATACTTTCCACCTAAAATT   1020
1021  CTGACAAGTGTTGGGTCTAATGTTTCTTTTCACTGCATCTATAAGAAGGAAAACAAGATT   1080
1081  GTTCCCTCAAAAGAGATTGTTTGGTGGATGAATTTAGCTGAGAAAATTCCTCAAAGCCAG   1140
1141  TATGATGTTGTGAGTGATCATGTTAGCAAAGTTACTTTTTTCAATCTGAATGAAACCAAA   1200
1201  CCTCGAGGAAAGTTTACCTATGATGCAGTGTACTGCTGCAATGAACATGAATGCCATCAT   1260
```

FIG. 4B

| | | |
|---|---|---|
| 1261 | CGCTATGCTGAATTATATGTGATTGATGTCAATATCAATATCTCATGTGAAACTGATGGG | 1320 |
| 1321 | TACTTAACTAAAATGACTTGCAGATGGTCAACCAGTACAATCCAGTCACTTGCGGAAAGC | 1380 |
| 1381 | ACTTTGCAATTGAGGTATCATAGGAGCAGCCTTTACTGTTCTGATATTCCATCTATTCAT | 1440 |
| 1441 | CCCATATCTGAGCCCAAAGATTGCTATTTGCAGAGTGATGGTTTTTATGAATGCATTTTC | 1500 |
| 1501 | CAGCCAATCTTCCTATTATCTGGCTACACAATGTGGATTAGGATCAATCACTCTCTAGGT | 1560 |
| 1561 | TCACTTGACTCTCCACCAACATGTGTCCTTCCTGATTCTGTGGTGAAGCCACTGCCTCCA | 1620 |
| 1621 | TCCAGTGTGAAAGCAGAAATTACTATAAACATTGGATTATTGAAAATATCTTGGGAAAAG | 1680 |
| 1681 | CCAGTCTTTCCAGAGAATAACCTTCAATTCCAGATTCGCTATGGTTTAAGTGGAAAAGAA | 1740 |
| 1741 | GTACAATGGAAGATGTATGAGGTTTATGATGCAAAATCAAAATCTGTCAGTCTCCCAGTT | 1800 |
| 1801 | CCAGACTTGTGTGCAGTCTATGCTGTTCAGGTGCGCTGTAAGAGGCTAGATGGACTGGGA | 1860 |
| 1861 | TATTGGAGTAATTGGAGCAATCCAGCCTACACAGTTGTCATGGATATAAAGTTCCTATG | 1920 |
| 1921 | AGAGGACCTGAATTTTGGAGAATAATTAATGGAGATACTATGAAAAAGGAGAAAAATGTC | 1980 |
| 1981 | ACTTTACTTTGGAAGCCCCTGATGAAAAATGACTCATTGTGCAGTGTTCAGAGATATGTG | 2040 |
| 2041 | ATAAACCATCATACTTCCTGCAATGGAACATGGTCAGAAGATGTGGGAAATCACACGAAA | 2100 |
| 2101 | TTCACTTTCCTGTGGACAGAGCAAGCACATACTGTTACGGTTCTGGCCATCAATTCAATT | 2160 |
| 2161 | GGTGCTTCTGTTGCAAATTTTAATTTAACCTTTTCATGGCCTATGAGCAAAGTAAATATC | 2220 |
| 2221 | GTGCAGTCACTCAGTGCTTATCCTTTAAACAGCAGTTGTGTGATTGTTTCCTGGATACTA | 2280 |
| 2281 | TCACCCAGTGATTACAAGCTAATGTATTTTATTATTGAGTGGAAAAATCTTAATGAAGAT | 2340 |
| 2341 | GGTGAAATAAAATGGCTTAGAATCTCTTCATCTGTTAAGAAGTATTATATCCATGGTAAG | 2400 |
| 2401 | TTTACTATACTTTAG | 2415 |

```
  1  M I C Q K F C V V L L H W E F I Y V I T   20
 21  A F N L S Y P I T P W R F K L S C M P P   40
 41  N S T Y D Y F L L P A G L S K N T S N S   60
 61  N G H Y E T A V E P K F N S S G T H F S   80
 81  N L S K T T F H C C F R S E Q D R N C S  100
101  L C A D N I E G K T F V S T V N S L V F  120
121  Q Q I D A N W N I Q C W L K G D L K L F  140
141  I C Y V E S L F K N L F R N Y N Y K V H  160
161  L L Y V L P E V L E D S P L V P Q K G S  180
181  F Q M V H C N C S V H E C C E C L V P V  200
201  P T A K L N D T L L M C L K I T S G G V  220
221  I F Q S P L M S V Q P I N M V K P D P P  240
241  L G L H M E I T D D G N L K I S W S S P  260
261  P L V P F P L Q Y Q V K Y S E N S T T V  280
281  I R E A D K I V S A T S L L V D S I L P  300
301  G S S Y E V Q V R G K R L D G P G I W S  320
321  D W S T P R V F T T Q D V I Y F P P K I  340
341  L T S V G S N V S F H C I Y K K E N K I  360
361  V P S K E I V W W M N L A E K I P Q S Q  380
381  Y D V V S D H V S K V T F F N L N E T K  400
401  P R G K F T Y D A V Y C C N E H E C H H  420
```

| | | | | | | | | | | | | | | | | | | | | | |
|---|---|---|---|---|---|---|---|---|---|---|---|---|---|---|---|---|---|---|---|---|---|
| 421 | R | Y | A | E | L | Y | V | I | D | V | N | I | N | I | S | C | E | T | D | G | 440 |
| 441 | Y | L | T | K | M | T | C | R | W | S | T | S | T | I | Q | S | L | A | E | S | 460 |
| 461 | T | L | Q | L | R | Y | H | R | S | S | L | Y | C | S | D | I | P | S | I | H | 480 |
| 481 | P | I | S | E | P | K | D | C | Y | L | Q | S | D | G | F | Y | E | C | I | F | 500 |
| 501 | Q | P | I | F | L | L | S | G | Y | T | M | W | I | R | I | N | H | S | L | G | 520 |
| 521 | S | L | D | S | P | P | T | C | V | L | P | D | S | V | V | K | P | L | P | P | 540 |
| 541 | S | S | V | K | A | E | I | T | I | N | I | G | L | L | K | I | S | W | E | K | 560 |
| 561 | P | V | F | P | E | N | N | L | Q | F | Q | I | R | Y | G | L | S | G | K | E | 580 |
| 581 | V | Q | W | K | M | Y | E | V | Y | D | A | K | S | K | S | V | S | L | P | V | 600 |
| 601 | P | D | L | C | A | V | Y | A | V | Q | V | R | C | K | R | L | D | G | L | G | 620 |
| 621 | Y | W | S | N | W | S | N | P | A | Y | T | V | V | M | D | I | K | V | P | M | 640 |
| 641 | R | G | P | E | F | W | R | I | I | N | G | D | T | M | K | K | E | K | N | V | 660 |
| 661 | T | L | L | W | K | P | L | M | K | N | D | S | L | C | S | V | Q | R | Y | V | 680 |
| 681 | I | N | H | H | T | S | C | N | G | T | W | S | E | D | V | G | N | H | T | K | 700 |
| 701 | F | T | F | L | W | T | E | Q | A | H | T | V | T | V | L | A | I | N | S | I | 720 |
| 721 | G | A | S | V | A | N | F | N | L | T | F | S | W | P | M | S | K | V | N | I | 740 |
| 741 | V | Q | S | L | S | A | Y | P | L | N | S | S | C | V | I | V | S | W | I | L | 760 |
| 761 | S | P | S | D | Y | K | L | M | Y | F | I | I | E | W | K | N | L | N | E | D | 780 |
| 781 | G | E | I | K | W | L | R | I | S | S | S | V | K | K | Y | Y | I | H | G | K | 800 |
| 801 | F | T | I | L | | | | | | | | | | | | | | | | | 804 |

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
(A) LENGTH: 54 base pairs
(B) TYPE: nucleic acid

-continued (C) STRANDEDNESS: single
(D) TOPOLOGY: linear (ii) MOLECULE TYPE: DNA (ix) FEATURE:
(A) NAME/KEY: CDS
(B) LOCATION: 1..54

(xi) SEQUENCE DESCRIPTION: SEQ ID NO:1:

```
AAT GTT AAA AAG TTT CAC ATC CAC GGT ATG TGT ACT GTA CTT TTC ATG       48
Asn Val Lys Lys Phe His Ile His Gly Met Cys Thr Val Leu Phe Met
  1               5                  10                  15

GAT TAG                                                               54
Asp  *
```

(2) INFORMATION FOR SEQ ID NO:2:

(i) SEQUENCE CHARACTERISTICS:
(A) LENGTH: 17 amino acids
(B) TYPE: amino acid
(D) TOPOLOGY: linear (ii) MOLECULE TYPE: protein (xi) SEQUENCE DESCRIPTION: SEQ ID NO:2:

```
Asn Val Lys Lys Phe His Ile His Gly Met Cys Thr Val Leu Phe Met
  1               5                  10                  15

Asp
```

(2) INFORMATION FOR SEQ ID NO:3:

(i) SEQUENCE CHARACTERISTICS:
(A) LENGTH: 44 amino acids
(B) TYPE: nucleic acid
(C) STRANDEDNESS: single
(D) TOPOLOGY: linear (ii) MOLECULE TYPE: DNA (ix) FEATURE:
(A) NAME/KEY: CDS
(B) LOCATION: 1..45

(xi) SEQUENCE DESCRIPTION: SEQ ID NO:3:

```
TCT GTT AAG AAG TAT TAT ATC CAT GGT AAG TTT ACT ATA CTT TAG           45
Ser Val Lys Lys Tyr Tyr Ile His Gly Lys Phe Thr Ile Leu
  1               5                  10                  15
```

(2) INFORMATION FOR SEQ ID NO:4:

(i) SEQUENCE CHARACTERISTICS:
(A) LENGTH: 14 amino acids
(B) TYPE: amino acid
(D) TOPOLOGY: linear (ii) MOLECULE TYPE: protein (xi) SEQUENCE DESCRIPTION: SEQ ID NO:4:

```
Ser Val Lys Lys Tyr Tyr Ile His Gly Lys Phe Thr Ile Leu
  1               5                  10                  15
```

(2) INFORMATION FOR SEQ ID NO:5:

(i) SEQUENCE CHARACTERISTICS:
(A) LENGTH: 26 amino acids
(B) TYPE: nucleic acid
(C) STRANDEDNESS: single
(D) TOPOLOGY: linear -continued (ii) MOLECULE TYPE: DNA (ix) FEATURE:
(A) NAME/KEY: CDS
(B) LOCATION: 1..27

(xi) SEQUENCE DESCRIPTION: SEQ ID NO:5:

```
GGT ATG TGT ACT GTA CTT TTC ATG GAT                                 27
Gly Met Cys Thr Val Leu Phe Met Asp
  1               5
```

(2) INFORMATION FOR SEQ ID NO:6:

(i) SEQUENCE CHARACTERISTICS:
(A) LENGTH: 9 amino acids
(B) TYPE: amino acid
(D) TOPOLOGY: linear (ii) MOLECULE TYPE: protein (xi) SEQUENCE DESCRIPTION: SEQ ID NO:6:

```
Gly Met Cys Thr Val Leu Phe Met Asp
  1               5
```

(2) INFORMATION FOR SEQ ID NO:7:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: CDS
(B) LOCATION: 1..18

(xi) SEQUENCE DESCRIPTION: SEQ ID NO:7:

```
GGT AAG TTT ACT ATA CTT                                             18
Gly Lys Phe Thr Ile Leu
 10                  15
```

(2) INFORMATION FOR SEQ ID NO:8:

(i) SEQUENCE CHARACTERISTICS:
(A) LENGTH: 6 amino acids
(B) TYPE: amino acid
(D) TOPOLOGY: linear (ii) MOLECULE TYPE: protein (xi) SEQUENCE DESCRIPTION: SEQ ID NO:8:

```
Gly Lys Phe Thr Ile Leu
  1               5
```

(2) INFORMATION FOR SEQ ID NO:9:

(i) SEQUENCE CHARACTERISTICS:
(A) LENGTH: 2415 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: CDS
(B) LOCATION: 1..2415

-continued

```
    (xi) SEQUENCE DESCRIPTION: SEQ ID NO:9:

ATG ATT TGT CAA AAA TTC TGT GTG GTT TTG TTA CAT TGG GAA TTT ATT         48
Met Ile Cys Gln Lys Phe Cys Val Val Leu Leu His Trp Glu Phe Ile
  1               5                  10                  15

TAT GTG ATA ACT GCG TTT AAC TTG TCA TAT CCA ATT ACT CCT TGG AGA         96
Tyr Val Ile Thr Ala Phe Asn Leu Ser Tyr Pro Ile Thr Pro Trp Arg
             20                  25                  30

TTT AAG TTG TCT TGC ATG CCA CCA AAT TCA ACC TAT GAC TAC TTC CTT        144
Phe Lys Leu Ser Cys Met Pro Pro Asn Ser Thr Tyr Asp Tyr Phe Leu
         35                  40                  45

TTG CCT GCT GGA CTC TCA AAG AAT ACT TCA AAT TCG AAT GGA CAT TAT        192
Leu Pro Ala Gly Leu Ser Lys Asn Thr Ser Asn Ser Asn Gly His Tyr
     50                  55                  60

GAG ACA GCT GTT GAA CCT AAG TTT AAT TCA AGT GGT ACT CAC TTT TCT        240
Glu Thr Ala Val Glu Pro Lys Phe Asn Ser Ser Gly Thr His Phe Ser
 65                  70                  75                  80

AAC TTA TCC AAA ACA ACT TTC CAC TGT TGC TTT CGG AGT GAG CAA GAT        288
Asn Leu Ser Lys Thr Thr Phe His Cys Cys Phe Arg Ser Glu Gln Asp
                 85                  90                  95

AGA AAC TGC TCC TTA TGT GCA GAC AAC ATT GAA GGA AAG ACA TTT GTT        336
Arg Asn Cys Ser Leu Cys Ala Asp Asn Ile Glu Gly Lys Thr Phe Val
            100                 105                 110

TCA ACA GTA AAT TCT TTA GTT TTT CAA CAA ATA GAT GCA AAC TGG AAC        384
Ser Thr Val Asn Ser Leu Val Phe Gln Gln Ile Asp Ala Asn Trp Asn
        115                 120                 125

ATA CAG TGC TGG CTA AAA GGA GAC TTA AAA TTA TTC ATC TGT TAT GTG        432
Ile Gln Cys Trp Leu Lys Gly Asp Leu Lys Leu Phe Ile Cys Tyr Val
    130                 135                 140

GAG TCA TTA TTT AAG AAT CTA TTC AGG AAT TAT AAC TAT AAG GTC CAT        480
Glu Ser Leu Phe Lys Asn Leu Phe Arg Asn Tyr Asn Tyr Lys Val His
145                 150                 155                 160

CTT TTA TAT GTT CTG CCT GAA GTG TTA GAA GAT TCA CCT CTG GTT CCC        528
Leu Leu Tyr Val Leu Pro Glu Val Leu Glu Asp Ser Pro Leu Val Pro
                165                 170                 175

CAA AAA GGC AGT TTT CAG ATG GTT CAC TGC AAT TGC AGT GTT CAT GAA        576
Gln Lys Gly Ser Phe Gln Met Val His Cys Asn Cys Ser Val His Glu
            180                 185                 190

TGT TGT GAA TGT CTT GTG CCT GTG CCA ACA GCC AAA CTC AAC GAC ACT        624
Cys Cys Glu Cys Leu Val Pro Val Pro Thr Ala Lys Leu Asn Asp Thr
        195                 200                 205

CTC CTT ATG TGT TTG AAA ATC ACA TCT GGT GGA GTA ATT TTC CAG TCA        672
Leu Leu Met Cys Leu Lys Ile Thr Ser Gly Gly Val Ile Phe Gln Ser
    210                 215                 220

CCT CTA ATG TCA GTT CAG CCC ATA AAT ATG GTG AAG CCT GAT CCA CCA        720
Pro Leu Met Ser Val Gln Pro Ile Asn Met Val Lys Pro Asp Pro Pro
225                 230                 235                 240

TTA GGT TTG CAT ATG GAA ATC ACA GAT GAT GGT AAT TTA AAG ATT TCT        768
Leu Gly Leu His Met Glu Ile Thr Asp Asp Gly Asn Leu Lys Ile Ser
                245                 250                 255

TGG TCC AGC CCA CCA TTG GTA CCA TTT CCA CTT CAA TAT CAA GTG AAA        816
Trp Ser Ser Pro Pro Leu Val Pro Phe Pro Leu Gln Tyr Gln Val Lys
            260                 265                 270

TAT TCA GAG AAT TCT ACA ACA GTT ATC AGA GAA GCT GAC AAG ATT GTC        864
Tyr Ser Glu Asn Ser Thr Thr Val Ile Arg Glu Ala Asp Lys Ile Val
        275                 280                 285

TCA GCT ACA TCC CTG CTA GTA GAC AGT ATA CTT CCT GGG TCT TCG TAT        912
Ser Ala Thr Ser Leu Leu Val Asp Ser Ile Leu Pro Gly Ser Ser Tyr
    290                 295                 300

GAG GTT CAG GTG AGG GGC AAG AGA CTG GAT GGC CCA GGA ATC TGG AGT        960
```

-continued

Glu Val Gln Val Arg Gly Lys Arg Leu Asp Gly Pro Gly Ile Trp Ser
305 310 315 320

GAC TGG AGT ACT CCT CGT GTC TTT ACC ACA CAA GAT GTC ATA TAC TTT 1008
Asp Trp Ser Thr Pro Arg Val Phe Thr Thr Gln Asp Val Ile Tyr Phe
325 330 335

CCA CCT AAA ATT CTG ACA AGT GTT GGG TCT AAT GTT TCT TTT CAC TGC 1056
Pro Pro Lys Ile Leu Thr Ser Val Gly Ser Asn Val Ser Phe His Cys
340 345 350

ATC TAT AAG AAG GAA AAC AAG ATT GTT CCC TCA AAA GAG ATT GTT TGG 1104
Ile Tyr Lys Lys Glu Asn Lys Ile Val Pro Ser Lys Glu Ile Val Trp
355 360 365

TGG ATG AAT TTA GCT GAG AAA ATT CCT CAA AGC CAG TAT GAT GTT GTG 1152
Trp Met Asn Leu Ala Glu Lys Ile Pro Gln Ser Gln Tyr Asp Val Val
370 375 380

AGT GAT CAT GTT AGC AAA GTT ACT TTT TTC AAT CTG AAT GAA ACC AAA 1200
Ser Asp His Val Ser Lys Val Thr Phe Phe Asn Leu Asn Glu Thr Lys
385 390 395 400

CCT CGA GGA AAG TTT ACC TAT GAT GCA GTG TAC TGC TGC AAT GAA CAT 1248
Pro Arg Gly Lys Phe Thr Tyr Asp Ala Val Tyr Cys Cys Asn Glu His
405 410 415

GAA TGC CAT CAT CGC TAT GCT GAA TTA TAT GTG ATT GAT GTC AAT ATC 1296
Glu Cys His His Arg Tyr Ala Glu Leu Tyr Val Ile Asp Val Asn Ile
420 425 430

AAT ATC TCA TGT GAA ACT GAT GGG TAC TTA ACT AAA ATG ACT TGC AGA 1344
Asn Ile Ser Cys Glu Thr Asp Gly Tyr Leu Thr Lys Met Thr Cys Arg
435 440 445

TGG TCA ACC AGT ACA ATC CAG TCA CTT GCG GAA AGC ACT TTG CAA TTG 1392
Trp Ser Thr Ser Thr Ile Gln Ser Leu Ala Glu Ser Thr Leu Gln Leu
450 455 460

AGG TAT CAT AGG AGC AGC CTT TAC TGT TCT GAT ATT CCA TCT ATT CAT 1440
Arg Tyr His Arg Ser Ser Leu Tyr Cys Ser Asp Ile Pro Ser Ile His
465 470 475 480

CCC ATA TCT GAG CCC AAA GAT TGC TAT TTG CAG AGT GAT GGT TTT TAT 1488
Pro Ile Ser Glu Pro Lys Asp Cys Tyr Leu Gln Ser Asp Gly Phe Tyr
485 490 495

GAA TGC ATT TTC CAG CCA ATC TTC CTA TTA TCT GGC TAC ACA ATG TGG 1536
Glu Cys Ile Phe Gln Pro Ile Phe Leu Leu Ser Gly Tyr Thr Met Trp
500 505 510

ATT AGG ATC AAT CAC TCT CTA GGT TCA CTT GAC TCT CCA CCA ACA TGT 1584
Ile Arg Ile Asn His Ser Leu Gly Ser Leu Asp Ser Pro Pro Thr Cys
515 520 525

GTC CTT CCT GAT TCT GTG GTG AAG CCA CTG CCT CCA TCC AGT GTG AAA 1632
Val Leu Pro Asp Ser Val Val Lys Pro Leu Pro Pro Ser Ser Val Lys
530 535 540

GCA GAA ATT ACT ATA AAC ATT GGA TTA TTG AAA ATA TCT TGG GAA AAG 1680
Ala Glu Ile Thr Ile Asn Ile Gly Leu Leu Lys Ile Ser Trp Glu Lys
545 550 555 560

CCA GTC TTT CCA GAG AAT AAC CTT CAA TTC CAG ATT CGC TAT GGT TTA 1728
Pro Val Phe Pro Glu Asn Asn Leu Gln Phe Gln Ile Arg Tyr Gly Leu
565 570 575

AGT GGA AAA GAA GTA CAA TGG AAG ATG TAT GAG GTT TAT GAT GCA AAA 1776
Ser Gly Lys Glu Val Gln Trp Lys Met Tyr Glu Val Tyr Asp Ala Lys
580 585 590

TCA AAA TCT GTC AGT CTC CCA GTT CCA GAC TTG TGT GCA GTC TAT GCT 1824
Ser Lys Ser Val Ser Leu Pro Val Pro Asp Leu Cys Ala Val Tyr Ala
595 600 605

GTT CAG GTG CGC TGT AAG AGG CTA GAT GGA CTG GGA TAT TGG AGT AAT 1872
Val Gln Val Arg Cys Lys Arg Leu Asp Gly Leu Gly Tyr Trp Ser Asn
610 615 620

-continued

```
TGG AGC AAT CCA GCC TAC ACA GTT GTC ATG GAT ATA AAA GTT CCT ATG      1920
Trp Ser Asn Pro Ala Tyr Thr Val Val Met Asp Ile Lys Val Pro Met
625                 630                 635                 640

AGA GGA CCT GAA TTT TGG AGA ATA ATT AAT GGA GAT ACT ATG AAA AAG      1968
Arg Gly Pro Glu Phe Trp Arg Ile Ile Asn Gly Asp Thr Met Lys Lys
                645                 650                 655

GAG AAA AAT GTC ACT TTA CTT TGG AAG CCC CTG ATG AAA AAT GAC TCA      2016
Glu Lys Asn Val Thr Leu Leu Trp Lys Pro Leu Met Lys Asn Asp Ser
            660                 665                 670

TTG TGC AGT GTT CAG AGA TAT GTG ATA AAC CAT CAT ACT TCC TGC AAT      2064
Leu Cys Ser Val Gln Arg Tyr Val Ile Asn His His Thr Ser Cys Asn
        675                 680                 685

GGA ACA TGG TCA GAA GAT GTG GGA AAT CAC ACG AAA TTC ACT TTC CTG      2112
Gly Thr Trp Ser Glu Asp Val Gly Asn His Thr Lys Phe Thr Phe Leu
    690                 695                 700

TGG ACA GAG CAA GCA CAT ACT GTT ACG GTT CTG GCC ATC AAT TCA ATT      2160
Trp Thr Glu Gln Ala His Thr Val Thr Val Leu Ala Ile Asn Ser Ile
705                 710                 715                 720

GGT GCT TCT GTT GCA AAT TTT AAT TTA ACC TTT TCA TGG CCT ATG AGC      2208
Gly Ala Ser Val Ala Asn Phe Asn Leu Thr Phe Ser Trp Pro Met Ser
                725                 730                 735

AAA GTA AAT ATC GTG CAG TCA CTC AGT GCT TAT CCT TTA AAC AGC AGT      2256
Lys Val Asn Ile Val Gln Ser Leu Ser Ala Tyr Pro Leu Asn Ser Ser
            740                 745                 750

TGT GTG ATT GTT TCC TGG ATA CTA TCA CCC AGT GAT TAC AAG CTA ATG      2304
Cys Val Ile Val Ser Trp Ile Leu Ser Pro Ser Asp Tyr Lys Leu Met
        755                 760                 765

TAT TTT ATT ATT GAG TGG AAA AAT CTT AAT GAA GAT GGT GAA ATA AAA      2352
Tyr Phe Ile Ile Glu Trp Lys Asn Leu Asn Glu Asp Gly Glu Ile Lys
    770                 775                 780

TGG CTT AGA ATC TCT TCA TCT GTT AAG AAG TAT TAT ATC CAT GGT AAG      2400
Trp Leu Arg Ile Ser Ser Ser Val Lys Lys Tyr Tyr Ile His Gly Lys
785                 790                 795                 800

TTT ACT ATA CTT TAG                                                  2415
Phe Thr Ile Leu  *
                805
```

(2) INFORMATION FOR SEQ ID NO:10:

(i) SEQUENCE CHARACTERISTICS:
(A) LENGTH: 804 amino acids
(B) TYPE: amino acid
(D) TOPOLOGY: linear (ii) MOLECULE TYPE: protein (xi) SEQUENCE DESCRIPTION: SEQ ID NO:10:

```
Met Ile Cys Gln Lys Phe Cys Val Val Leu Leu His Trp Glu Phe Ile
  1               5                  10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
     50                  55                  60

Glu Thr Ala Val Glu Pro Lys Phe Asn Ser Ser Gly Thr His Phe Ser
 65                  70                  75                  80

Asn Leu Ser Lys Thr Thr Phe His Cys Cys Phe Arg Ser Glu Gln Asp
                 85                  90                  95

Arg Asn Cys Ser Leu Cys Ala Asp Asn Ile Glu Gly Lys Thr Phe Val
```

-continued

```
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
    210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
        275                 280                 285

Ser Ala Thr Ser Leu Leu Val Asp Ser Ile Leu Pro Gly Ser Ser Tyr
    290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
        355                 360                 365

Trp Met Asn Leu Ala Glu Lys Ile Pro Gln Ser Gln Tyr Asp Val Val
    370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
        435                 440                 445

Trp Ser Thr Ser Thr Ile Gln Ser Leu Ala Glu Ser Thr Leu Gln Leu
    450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Pro Thr Cys
        515                 520                 525
```

-continued

```
Val Leu Pro Asp Ser Val Val Lys Pro Leu Pro Pro Ser Ser Val Lys
    530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Cys Ala Val Tyr Ala
        595                 600                 605

Val Gln Val Arg Cys Lys Arg Leu Asp Gly Leu Gly Tyr Trp Ser Asn
    610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
        675                 680                 685

Gly Thr Trp Ser Glu Asp Val Gly Asn His Thr Lys Phe Thr Phe Leu
    690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
        755                 760                 765

Tyr Phe Ile Ile Glu Trp Lys Asn Leu Asn Glu Asp Gly Glu Ile Lys
    770                 775                 780

Trp Leu Arg Ile Ser Ser Ser Val Lys Lys Tyr Tyr Ile His Gly Lys
785                 790                 795                 800

Phe Thr Ile Leu
                805
```

(2) INFORMATION FOR SEQ ID NO:11:

(i) SEQUENCE CHARACTERISTICS:
(A) LENGTH: 36 amino acids
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:11:

```
CGCGGATCCA TTATGTCTGC ACTCCGAAGG AAATTTG                          37
```

(2) INFORMATION FOR SEQ ID NO:12:

(i) SEQUENCE CHARACTERISTICS:
(A) LENGTH: 37 amino acids
(B) TYPE: nucleic acid
(C) STRANDEDNESS: single
(D) TOPOLOGY: linear -continued (ii) MOLECULE TYPE: other nucleic acid (xi) SEQUENCE DESCRIPTION: SEQ ID NO:12:

CGCGAATTCT TATGTGAAGC GATCAGAGTT CATTTTTC 38

(2) INFORMATION FOR SEQ ID NO:13:

(i) SEQUENCE CHARACTERISTICS:
(A) LENGTH: 33 amino acids
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:13:

GCGGGATCCG CTATGGCTGG TGATTCTAGG AATG 34

(2) INFORMATION FOR SEQ ID NO:14:

(i) SEQUENCE CHARACTERISTICS:
(A) LENGTH: 28 amino acids
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:14:

CCGGAATTCC CCTCACACCG AGCCCCTGG 29

(2) INFORMATION FOR SEQ ID NO:15:

(i) SEQUENCE CHARACTERISTICS:
(A) LENGTH: 25 amino acids
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:15:

CAGGTGAGGG GCAAGAGACT GGATGG 26

(2) INFORMATION FOR SEQ ID NO:16:

(i) SEQUENCE CHARACTERISTICS:
(A) LENGTH: 26 amino acids
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:16:

CAAGCACATA CTGTTACGGT TCTGGCA 27

(2) INFORMATION FOR SEQ ID NO:17:

(i) SEQUENCE CHARACTERISTICS:
(A) LENGTH: 25 amino acids
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:17:

-continued

CCCAAGAATT GTTCCTGGGC ACAAGG 26

(2) INFORMATION FOR SEQ ID NO:18:

(i) SEQUENCE CHARACTERISTICS:
(A) LENGTH: 28 amino acids
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:18:

CCATGAAAAG TACAGTACAC ATACCATGG 29

(2) INFORMATION FOR SEQ ID NO:19:

(i) SEQUENCE CHARACTERISTICS:
(A) LENGTH: 24 amino acids
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:19:

CCTGAGCAGC AGCTGTGTCA TCCTT 25

(2) INFORMATION FOR SEQ ID NO:20:

(i) SEQUENCE CHARACTERISTICS:
(A) LENGTH: 25 amino acids
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:20:

GCGTCATTCT GCTGCTTGTC GATAGC 26

(2) INFORMATION FOR SEQ ID NO:21:

(i) SEQUENCE CHARACTERISTICS:
(A) LENGTH: 25 amino acids
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:21:

GGGTAAAGAC TGAACTGGTA CTTCTC 26

(2) INFORMATION FOR SEQ ID NO:22:

(i) SEQUENCE CHARACTERISTICS:
(A) LENGTH: 24 amino acids
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:22:

CTAAAGTATA GTAAACTTAC CATGG 25

(2) INFORMATION FOR SEQ ID NO:23:

-continued (i) SEQUENCE CHARACTERISTICS:
(A) LENGTH: 28 amino acids
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:23:

GGATTATATG TATTAGGATG GTAGTATCC 29

(2) INFORMATION FOR SEQ ID NO:24:

(i) SEQUENCE CHARACTERISTICS:
(A) LENGTH: 54 amino acids
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:24:

TCTGTTAAGA AGTATTATAT CCATGGTAAG TTTACTATAC TTTAGTAATG AATGA 55

(2) INFORMATION FOR SEQ ID NO:25:

(i) SEQUENCE CHARACTERISTICS:
(A) LENGTH: 55 amino acids
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:25:

AGCTTCATTC ATTACTAAAG TATAGTAAAC TTACCATGGA TATAATACTT CTTAAC 56

(2) INFORMATION FOR SEQ ID NO:26:

(i) SEQUENCE CHARACTERISTICS:
(A) LENGTH: 25 amino acids
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:26:

ATCGTGCAGT CACTCAGTGC TTATCC 26

(2) INFORMATION FOR SEQ ID NO:27:

(i) SEQUENCE CHARACTERISTICS:
(A) LENGTH: 29 amino acids
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:27:

GGCCATCAAT TCAATTGGTG CTTCTGTTGC 30

(2) INFORMATION FOR SEQ ID NO:28:

(i) SEQUENCE CHARACTERISTICS:
(A) LENGTH: 28 amino acids
(B) TYPE: nucleic acid

-continued

```
        (C) STRANDEDNESS: single
        (D) TOPOLOGY: linear

    (ii) MOLECULE TYPE: DNA

    (xi) SEQUENCE DESCRIPTION: SEQ ID NO:28:

GGAGCAATCC AGCCTACACA GTTGTCATG                                     29


(2) INFORMATION FOR SEQ ID NO:29:

     (i) SEQUENCE CHARACTERISTICS:
        (A) LENGTH:  26 amino acids
        (B) TYPE: nucleic acid
        (C) STRANDEDNESS: single
        (D) TOPOLOGY: linear

    (ii) MOLECULE TYPE: DNA

    (xi) SEQUENCE DESCRIPTION: SEQ ID NO:29:

CCTGCAATGG AACATGGTCA GAAGATG                                       27
```

METHODS OF IDENTIFYING OR SCREENING FOR AGENTS THAT BINDS THE OB-RE

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citations for these references may be found at the end of this application, preceding the sequence listing and the claims.

The ob gene has recently been cloned and shown to encode a 146 amino acid protein called leptin which is secreted into the blood exclusively by white fat adipocytes. The leptin receptor has also recently been cloned and shown to exist as several splice variants. The functional splice variant (Ob-Rb) is present in several tissues including hypothalamus, adipocytes and kidney. The short form splice variant (Ob-Ra) has a more ubiquitous tissue distribution and is more abundant than the functional splice variant. The role of Ob-Ra is unknown but this splice variant may serve as a leptin transport system in choroid plexus, kidney and perhaps also the lung. A third major splice variant (Ob-Re) has also been described in mice which encodes only the extracellular domain of the receptor, giving rise to a soluble protein in the circulation which may function there as a leptin binding/buffering system.

Circulating leptin acts as an antiobesity agent by restraining appetite and altering metabolic processes to burn fat. The hypothalamus appears to be the major target tissue for the hormone since leptin receptors are present there and intracerebroventricular injection of leptin leads to a reduction of food intake. Recent evidence suggests that at least part of the reduction in food intake produced by leptin may be due to a decrease in central neuropeptide Y. It is unclear whether the changes in metabolism produced by leptin are mediated by actions only on the brain or also involve direct effects upon peripheral tissues. Although the mechanism of action has not been fully elucidated, leptin may be the long sought after satiety factor released from the periphery (i.e. the adipocytes) to regulate long-term body weight. As body weight and fat mass increase, more leptin is secreted which may inhibit appetite and increase metabolism to bring the fat mass back to a certain set point. The incapacity to express a functional leptin is the cause of obesity in the ob/ob mouse. Defects in the functional leptin receptor such as those found in the db/db mouse and the fa/fa rat are responsible for the obesity observed in these animal models.

The observation that obese animals and man, although having high plasma leptin levels remain overweight, may suggest the development of 'resistance' to the actions of leptin. This may occur at the level of the brain and be due to saturation of the leptin uptake system. Alternatively, 'resistance' may be due to the presence of a circulating binding protein which by buffering leptin might reduce its actions.

The single gene defects of rodents described above may play only a minor role in human obesity. However, leptin is present in man, thus, pharmacological stimulation of the leptin pathway has the potential to reduce body weight in man by inhibiting food intake and diminishing the size of the body fat stores. Such therapeutic interventions could be achieved either by enhancing leptin release from the adipocytes, preventing the breakdown or clearance of leptin, preventing interaction of leptin binding to the soluble binding protein, by administration of leptin mimics or by stimulating events downstream of the leptin receptor. On the other hand, pharmacological inhibition of leptin action or production may have the potential to increase food intake and body weight in man. Evidence to support this comes from the ob/ob and db/db mouse and the fa/fa rat in which the actions of leptin are not apparent. These animals are obese and hyperphagic. Applicants now report the isolation of a novel human Ob-Re receptor, referred to herein as "hOb-Re" or the "polypeptide." This discovery provides a novel approach to the treatment of eating disorders, both by therapeutic administration of the soluble human Ob-Re receptor to subjects suffering from such disorders, and through the use of heterologous expression systems to develop high-affinity compounds that could serve as therapeutic agents for such disorders.

SUMMARY OF THE INVENTION

This invention is directed to an isolated nucleic acid which encodes a polypeptide comprising the amino acid sequence shown in FIG. 5 (Seq. I.D. No. 10) or a polypeptide having a sequence which varies therefrom by no more than 15 amino acids, such amino acid variations not involving amino acid positions 799–804 and not changing the functional properties of the polypeptide.

This invention is additionally directed to a nucleic acid which comprises the nucleic acid of above linked to a nucleic acid encoding a polypeptide corresponding to an artificial transmembrane region of a receptor which is not an Ob receptor.

This invention is additionally directed to a nucleic acid which comprises the nucleic acid of above linked to nucleic acid encoding a polypeptide corresponding to an artificial intracellular domain of a receptor which is not an Ob receptor.

This invention is additionally directed to purified polypeptides encoded by the nucleic acid of this invention.

This invention is additionally directed to vectors comprising the nucleic acid of this invention.

This invention is additionally directed to cells comprising the vector of this invention.

This invention is additionally directed to a membrane preparation isolated from the cell of this invention.

This invention is additionally directed to a nucleic acid probe comprising at least 15 nucleotides, which probe has a unique sequence corresponding to a sequence present within (a) the nucleic acid sequence from nucleotide number 2395 through nucleotide number 2412 of FIG. 4 (Seq. I.D. No. 9) or (b) a reverse complement thereof.

This invention is additionally directed to an antisense oligonucleotide having a unique sequence corresponding to a sequence present within (a) the nucleic acid sequence from nucleotide number 2395 through nucleotide number 2412 of FIG. 4 (Seq. I.D. No. 9) or (b) a reverse complement thereof.

This invention is additionally directed to an antibody capable of specifically binding to the polypeptide containing at least a unique sequence corresponding to a sequence present within the amino acid sequence from amino acid number 799 through amino acid number 804 of FIG. 5 (Seq. I.D. No. 10).

This invention is additionally directed to a pharmaceutical composition comprising an amount of the oligonucleotide effective to reduce expression of a polypeptide and a pharmaceutically acceptable carrier.

This invention is additionally directed to a pharmaceutical composition which comprises an amount of the antibody effective to block binding of a ligand to the polypeptide and a pharmaceutically acceptable carrier.

This invention is additionally directed to a transgenic nonhuman mammal expressing a nucleic acid of this invention.

This invention is directed to a process for identifying a chemical compound which specifically binds to a polypeptide of this invention, which comprises contacting the polypeptide with the compound under conditions suitable for binding, and detecting specific binding of the chemical compound to the polypeptide.

This invention is additionally directed to a process involving competitive binding for identifying a chemical compound which specifically binds to a polypeptide of this invention which comprises separately contacting the polypeptide, with both the chemical compound and a second chemical compound known to bind to the polypeptide, and with only the second chemical compound, under conditions suitable for binding of both compounds, and detecting specific binding of the chemical compound to the polypeptide, a decrease in the binding of the second chemical compound to the polypeptide in the presence of the chemical compound indicating that the chemical compound binds to the polypeptide.

This invention is additionally directed to a process for identifying a chemical compound which specifically binds to a polypeptide encoded by a nucleic acid of this invention, which comprises contacting cells containing DNA encoding and expressing on the cell surface the polypeptide, with the compound under conditions suitable for binding, and detecting specific binding of the chemical compound to the polypeptide.

This invention is directed to a process for identifying a chemical compound which specifically binds to a polypeptide encoded by a nucleic acid of this invention, which comprises contacting a membrane fraction from a cell extract of cells containing DNA encoding and expressing on their cell surface the polypeptide, with the compound under conditions suitable for binding, and detecting specific binding of the chemical compound to the polypeptide.

This invention is directed to a process involving competitive binding for identifying a chemical compound which specifically binds to a polypeptide encoded by a nucleic acid of this invention, which comprises separately contacting cells expressing on their cell surface the polypeptide, with both the chemical compound and a second chemical compound known to bind to the polypeptide, and with only the second chemical compound, under conditions suitable for binding of both compounds, and detecting specific binding of the chemical compound to the polypeptide, a decrease in the binding of the second chemical compound to the polypeptide in the presence of the chemical compound indicating that the chemical compound binds to the polypeptide.

This invention is directed to a process involving competitive binding for identifying a chemical compound which specifically binds to a polypeptide encoded by a nucleic acid of this invention, which comprises separately contacting a membrane fraction from a cell extract of cells expressing on their cell surface the polypeptide, with both the chemical compound and a second chemical compound known to bind to the polypeptide, and with only the second chemical compound, under conditions suitable for binding of both compounds, and detecting specific binding of the chemical compound to the polypeptide, a decrease in the binding of the second chemical compound to the polypeptide in the presence of the chemical compound indicating that the chemical compound binds to the polypeptide.

This invention is directed to a method of screening a plurality of chemical compounds not known to bind to a polypeptide encoded by a nucleic acid of this invention to identify a compound which specifically binds to the polypeptide, which comprises:

(a) contacting cells transfected with and expressing DNA encoding the polypeptide with a compound known to bind specifically to the polypeptide;

(b) contacting the preparation of step (a) with the plurality of compounds not known to bind specifically to the polypeptide, under conditions permitting binding of compounds known to bind the polypeptide;

(c) determining whether the binding of the compound known to bind to the polypeptide is reduced in the presence of the plurality of compounds, relative to the binding of the compound in the absence of the plurality of compounds; and if so (d) separately determining the binding to the polypeptide of each compound included in the plurality of compounds, so as to thereby identify the compound which specifically binds to the polypeptide.

This invention is directed to a method of screening a plurality of chemical compounds not known to bind to a polypeptide of this invention to identify a compound which specifically binds to the polypeptide, which comprises:

(a) preparing a cell extract or cell supernatant from cells transfected with and expressing DNA encoding the polypeptide and contacting the cell extract or cell supernatant with a compound known to bind specifically to the polypeptide;

(b) contacting the preparation of step (a) with the plurality of compounds not known to bind specifically to the polypeptide, under conditions permitting binding of compounds known to bind the polypeptide;

(c) determining whether the binding of the compound known to bind to the polypeptide is reduced in the presence of the compounds, relative to the binding of the compound in the absence of the plurality of compounds; and if so (d) separately determining the binding to the polypeptide of each compound included in the plurality of compounds, so as to thereby identify the compound which specifically binds to the polypeptide.

This invention is directed to a process for determining whether a chemical compound is an Ob receptor agonist which comprises contacting cells transfected with and expressing DNA of this invention with the compound under conditions permitting the activation of the Ob receptor, and detecting an increase in Ob receptor activity, so as to thereby determine whether the compound is an Ob receptor agonist.

This invention is directed to a process for determining whether a chemical compound is an Ob receptor agonist which comprises preparing a cell extract from cells transfected with and expressing DNA of this invention, isolating a membrane fraction from the cell extract, contacting the membrane fraction with the compound under conditions permitting the activation of the Ob receptor, and detecting an increase in Ob receptor activity, so as to thereby determine whether the compound is an Ob receptor agonist.

This invention is directed to a process for determining whether a chemical compound is an Ob receptor antagonist which comprises contacting cells transfected with and expressing DNA of this invention with the compound in the presence of a known Ob receptor agonist, under conditions permitting the activation of an Ob receptor, and detecting a decrease in Ob receptor activity, so as to thereby determine whether the compound is an Ob receptor antagonist.

This invention is directed to a process for determining whether a chemical compound is an Ob receptor antagonist which comprises preparing a cell extract from cells transfected with and expressing DNA of this invention, isolating a membrane fraction from the cell extract, contacting the membrane fraction with the ligand in the presence of a known Ob receptor agonist, under conditions permitting the activation of the Ob receptor, and detecting a decrease in Ob receptor activity, so as to thereby determine whether the compound is an Ob receptor antagonist.

This invention is directed to a pharmaceutical composition comprising an effective amount of a polypeptide of this invention and a pharmaceutically acceptable carrier.

This invention is directed to a method for determining whether a compound modulates leptin activity which comprises:

(a) administering to an animal a polypeptide of this invention and measuring the amount of food intake, metabolic, or body weight changes in the animal;

(b) administering to a second animal both the polypeptide and the compound, and measuring the amount of food intake, metabolic, or body weight changes in the second animal; and (c) determining whether the amount of food intake, metabolic, or body weight change is altered in the presence of the compound relative to the amount of food intake, metabolic, or body weight change in the absence of the compound, so as to thereby determine whether the compound modulates leptin activity.

This invention is directed to a method of screening a plurality of compounds to identify a compound which modulates leptin activity which comprises:

(a) administering to an animal a polypeptide of this invention and measuring the amount of food intake, metabolic, or body weight changes in the animal;

(b) administering to a second animal the polypeptide and at least one compound of the plurality of compounds and measuring the amount of food intake, metabolic, or body weight changes in the animal;

(c) determining whether the amount of food intake, metabolic, or body weight change is altered in the presence of at least one compound of the plurality relative to the amount of food intake, metabolic, or body weight change in the absence of at least one compound of the plurality, and if so;

(d) separately determining whether each compound modulates leptin activity according to the method of this invention, so as to thereby identify a compound which modulates leptin activity.

This invention is directed to a method of treating an abnormality in a subject, wherein the abnormality is alleviated by modulating the activity of leptin in the subject, which comprises administering to a subject an amount of the pharmaceutical composition of this invention effective to modulate the activity of leptin in the subject, thereby treating the abnormality in the subject.

This invention is directed to a method of modulating feeding behavior or metabolism of a subject which comprises administering to the subject an amount of a polypeptide of this invention effective to modulate the feeding behavior or metabolism of the subject so as to thereby modulate feeding behavior or metabolism of the subject.

This invention is directed to a method of modulating feeding behavior or metabolism of a subject which comprises administering a polypeptide of this invention and a compound which binds to the Y5 receptor, the amount of such polypeptide and compound being effective to modulate the feeding behavior or metabolism of the subject.

This invention is directed to a method of modulating feeding behavior or metabolism in a subject which comprises administering to the subject an amount of a compound which binds to a polypeptide of this invention effective to alter the activity of leptin in the subject, so as to thereby modulate feeding behavior or metabolism of the subject.

This invention is directed to a method of modulating feeding behavior or metabolism of a subject which comprises administering a compound which binds to a polypeptide of this invention and a second compound which binds to the Y5 receptor, the amount of the first compound and the second compound being effective to modulate the feeding behavior or metabolism of the subject.

This invention is directed to a method of detecting expression of a polypeptide of this invention by detecting the presence of mRNA coding for the polypeptide which comprises obtaining total mRNA from the cell and contacting the mRNA so obtained with the nucleic acid probe of this invention under hybridizing conditions, detecting the presence of mRNA hybridized to the probe, and thereby detecting the expression of the polypeptide by the cell.

This invention is directed to a method of detecting the presence of a polypeptide which comprises contacting the cell or cell supernatant with the antibody of this invention under conditions permitting binding of the antibody to the polypeptide, detecting the presence of the antibody bound to the cell or cell supernatant, and thereby detecting the presence of a polypeptide.

This invention is directed to a method of determining the physiological effects of varying levels of activity of polypeptides which comprises producing a transgenic nonhuman mammal of this invention whose levels of polypeptide activity are varied by use of an inducible promoter which regulates polypeptide expression.

This invention is directed to a method of determining the physiological effects of varying levels of activity of polypeptides which comprises producing a panel of transgenic nonhuman mammals of this invention each expressing a different amount of polypeptide.

This invention is directed to a method for diagnosing a predisposition to a disorder associated with the activity of a specific polypeptide allele which comprises:

(a) obtaining DNA of subjects suffering from the disorder;

(b) performing a restriction digest of the DNA with a panel of restriction enzymes;

(c) electrophoretically separating the resulting DNA fragments on a sizing gel;

(d) contacting the resulting gel with a nucleic acid probe capable of specifically hybridizing with a unique sequence included within the sequence of a nucleic acid molecule encoding a polypeptide and labeled with a detectable marker;

(e) detecting labeled bands which have hybridized to the nucleic acid of this invention labeled with a detectable marker to create a unique band pattern specific to the DNA of subjects suffering from the disorder;

(f) preparing DNA obtained for diagnosis by steps a–e; and (g) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention is directed to a method of preparing the purified polypeptide of this invention which comprises:

(a) inducing cells to express the polypeptide;

(b) recovering the polypeptide from the induced cells; and (c) purifying the polypeptide so recovered.

This invention is directed to a method of preparing the purified polypeptide of this invention which comprises:

(a) inserting nucleic acid encoding the polypeptide in a suitable vector;

(b) introducing the resulting vector in a suitable host cell;

(c) placing the resulting cell in suitable condition permitting the production of the isolated polypeptide;

(d) recovering the polypeptide produced by the resulting cell; and (e) purifying the polypeptide so recovered.

BRIEF DESCRIPTION OF THE FIGURES

FIG. 2*a*: The mOb-Re-specific sequence may be encoded by an exon that is contiguous to the 3'-most common exon. FIG. 2*b*: The mOb-Re-specific sequence may be encoded by an unspliced intron. The asterisk represents the stop codon in mOb-Re.

FIGS. 3*a* and 3*b* FIG. 3*a*: Nucleotide sequence and deduced amino acid sequence (Seq. I.D. Nos.: 1 and 2, respectively) of mouse genomic DNA, and nucleotide and deduced amino acid sequence (Seq. I.D. Nos.: 3 and 4, respectively) of human genomic DNA across the intron-exon border of the 3' most common exon. Residues in normal type represent the 3' end of the exon, and residues in bold represent the 5' end of the intron. The mouse sequence in bold is identical to the published mOb-Re sequence. The human sequence in bold is the hOb-Re-specific sequence. FIG. 3*b*: Comparison of the mouse Ob-Re-specific nucleotide and amino acid sequence (Seq. I.D. Nos.: 5 and 6, respectively) with the human Ob-Re-specific nucleotide and amino acid sequences (Seq. I.D. Nos.: 7 and 8, respectively). Underlined residues are conserved across the species.

FIGS. 4*a*–4*b* Nucleotide coding sequence of the human Ob-Re receptor (Seq. I.D. No. 9), including stop codon (TAG).

FIGS. 5*a*–5*b* Deduced amino acid sequence of the human Ob-Re receptor (Seq. I.D. No. 10) encoded by the human nucleotide sequence shown in FIG. 4.

FIG. 6*a*: The hOb-Re-specific sequence may be encoded by an exon that is contiguous to the 3'-most common exon. FIG. 6*b*: The hOb-Re-specific sequence may be encoded by an unspliced intron. The asterisk represents the stop codon in hOb-Re.

(FIG. 10*b*), 96 hours. (FIG. 10*c*) and 120 hrs (FIG. 10*d*) post-infection were evaluated. Results are means±S.E.M. of triplicate determinations expressed as cpm bound/well. "Wt" indicates wild type and "Un" indicates untransfected.

DETAILED DESCRIPTION OF THE INVENTION

Figure 1:
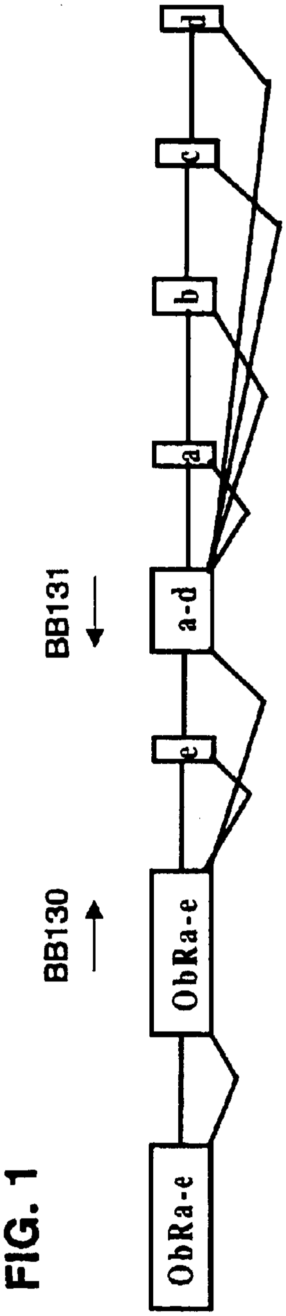
FIG. 1 Schematic of the likely genomic structure for the 3' end of the mouse Ob-R gene based on previous findings. Boxes represent exons, horizontal lines represent introns, and diagonal lines indicate exon splicing. The first two exons shown represent the two 3'-most exons that are common to all splice variants. The fourth exon shown represents an exon common to all splice variants other than Ob-Re. The remaining exons are specific for individual splice variants. Primers in exons believed to be immediately upstream (BB130) and downstream (BB131) of the mOb-Re-specific exon are shown.

Throughout this application, the following standard abbreviations are used to indicate specific nucleotide bases:

| C = cytosine | A = adenine |
|---|---|
| T = thymine | G = guanine |

This invention is directed to an isolated nucleic acid which encodes a polypeptide comprising the amino acid sequence shown in FIG. 5 (Seq. I.D. No. 10) or a polypeptide having a sequence which varies therefrom by no more than 15 amino acids (preferably no more than 10 amino acids and more preferably no more than 5 amino acids), such amino acid variations not involving amino acid positions 799–804 and not changing the functional properties of the polypeptide. In regard to the foregoing, variations include additions, deletions, substitutions or combinations thereof.

In one embodiment, nucleic acid encodes a polypeptide having the amino acid sequence shown in FIG. 5 (Seq. I.D. No. 10).

In another embodiment, the nucleic acid is DNA. In another embodiment, the DNA is cDNA. In another embodiment, the DNA is genomic DNA. In another embodiment, the nucleic acid is RNA. In another embodiment, the nucleic acid is linked to a nucleic acid encoding a flag epitope.

This invention is directed to a nucleic acid which comprises the nucleic acid of this invention linked to a nucleic acid encoding a polypeptide corresponding to an artificial transmembrane region of a receptor which is not an Ob receptor.

This invention is directed to a nucleic acid which comprises the nucleic acid of this invention linked to nucleic acid encoding a polypeptide corresponding to an artificial intracellular domain of a receptor which is not an Ob receptor.

Heterologous expression systems utilizing appropriate host cells to express the nucleic acid of the subject invention are used to obtain the desired cellular response.

This invention is directed to a purified polypeptide encoded by the nucleic acid of this invention.

The polypeptides described hereinabove may be transfected into cells either transiently or stably using methods well-known in the art, examples of which are disclosed herein. This invention further provides for a compound identified using a polypeptide in a binding assay such as the binding assays described herein.

In another embodiment, the nucleic acid encoding the polypeptide comprises an intron. In still another embodiment, the nucleic acid encoding the polypeptide comprises alternately spliced nucleic acid. The existence and use of alternative exons is possible, whereby the mRNA may encode different amino acids within the region comprising the exon. In addition, single amino acid substitutions may arise via the mechanism of RNA editing such that the amino acid sequence of the expressed polypeptide is different than that encoded by the original gene (Burns et al., 1996; Chu et al., 1996). Such variants may exhibit pharmacologic properties differing from the polypeptide encoded by the original gene. This invention provides a splice variant of the polypeptides disclosed herein. This invention further provides for alternate translation initiation sites and alternately spliced or edited variants of nucleic acids encoding the polypeptides.

This invention provides the above-described isolated nucleic acids, wherein the nucleic acid is DNA. In an embodiment, the DNA is cDNA. In another embodiment, the DNA is genomic DNA. In still another embodiment, the nucleic acid molecule is RNA. Methods for production and manipulation of nucleic acid molecules are well known in the art This invention is directed to a vector comprising the nucleic acid of this invention.

In one embodiment, the vector is adapted for expression in a bacterial cell which comprises the regulatory elements necessary for expression of the nucleic acid in the bacterial cell operatively linked to the nucleic acid encoding the polypeptide so as to permit expression thereof.

In another embodiment, the vector is adapted for expression in a yeast cell which comprises the regulatory elements necessary for expression of the nucleic acid in the yeast cell operatively linked to the nucleic acid encoding the polypeptide so as to permit expression thereof.

In another embodiment, the vector is adapted for expression in an insect cell which comprises the regulatory elements necessary for expression of the nucleic acid in the insect cell operatively linked to the nucleic acid encoding the polypeptide so as to permit expression thereof.

In another embodiment, the vector is a baculovirus vector.

In another embodiment, the baculovirus vector is designated Bac-BO45 (ATCC Accession No. VR-2574).

In another embodiment, the vector is adapted for expression in an amphibian cell which comprises the regulatory elements necessary for expression of the nucleic acid in the amphibian cell operatively linked to the nucleic acid encoding the polypeptide so as to permit expression thereof.

In another embodiment, the vector is adapted for expression in a mammalian cell which comprises the regulatory elements necessary for expression of the nucleic acid in the mammalian cell operatively linked to the nucleic acid encoding the polypeptide so as to permit expression thereof.

This invention is directed to a plasmid vector of this invention.

In one embodiment, the plasmid vector is adapted for expression in a mammalian cell which comprises the regulatory elements necessary for expression of the nucleic acid in the mammalian cell operatively linked to the nucleic acid encoding the polypeptide so as to permit expression thereof.

In one embodiment, the plasmid vector is designated BO-25 (ATCC Accession No. 209036).

In another embodiment, the vector comprises the nucleic acid of this invention.

In another embodiment, the vector is adapted for expression in a bacterial cell which comprises the regulatory elements necessary for expression of the nucleic acid in the bacterial cell operatively linked to the nucleic acid encoding the polypeptide so as to permit expression thereof.

In another embodiment, the vector is adapted for expression in a yeast cell which comprises the regulatory elements necessary for expression of the nucleic acid in the yeast cell operatively linked to the nucleic acid encoding the polypeptide so as to permit expression thereof.

In another embodiment, the vector is adapted for expression in an insect cell which comprises the regulatory elements necessary for expression of the nucleic acid in the insect cell operatively linked to the nucleic acid encoding the polypeptide so as to permit expression thereof.

This invention is directed to a baculovirus vector of this invention.

In another embodiment, the vector is adapted for expression in an amphibian cell which comprises the regulatory elements necessary for expression of the nucleic acid in the amphibian cell operatively linked to the nucleic acid encoding the polypeptide so as to permit expression thereof.

In another embodiment, the vector is adapted for expression in a mammalian cell which comprises the regulatory elements necessary for expression of the nucleic acid in the mammalian cell operatively linked to the nucleic acid encoding the polypeptide so as to permit expression thereof.

This invention is directed to a plasmid vector of this invention.

In one embodiment, the plasmid vector of this invention adapted for expression in a mammalian cell which comprises the regulatory elements necessary for expression of the nucleic acid in the mammalian cell operatively linked to the nucleic acid encoding the polypeptide so as to permit expression thereof.

This invention further provides nucleic acid which is degenerate with respect to DNA encoding any of the above-described polypeptides. In an embodiment, the nucleic acid comprises a nucleotide sequence which is degenerate with respect to the nucleotide sequence shown in FIG. 4 (Seq. I.D. No. 9) or in plasmid BO-25, that is, a nucleotide sequence which is translated into the same amino acid sequence.

This invention also encompasses DNAs and cDNAs which encode amino acid sequences which differ from those of the above-described polypeptides, but which should not Produce phenotypic changes. Alternatively, this invention also encompasses DNAs, cDNAs, and RNAs which hybridize to the DNA, cDNA, and RNA of the subject invention. Hybridization methods are well known to those of skill in the art.

The nucleic acids of the subject invention also include nucleic acid molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons “preferred” for expression by selected non-mammalian hosts; the provision of sites for cleavage by restriction endonuclease enzymes; and the provision of additional initial, terminal or intermediate DNA sequences that facilitate construction of readily expressed vectors.

The modified polypeptides described hereinabove may be transfected into cells either transiently or stably using methods well-known in the art, examples of which are disclosed herein. This invention further provides for a compound identified using a polypeptide in a binding assay such as the binding assays described herein.

The nucleic acids described and claimed herein are useful for the information which they provide concerning the amino acid sequence of the polypeptide and as products for the large scale synthesis of the polypeptide by a variety of recombinant techniques. The nucleic acid molecule is useful for generating new cloning and expression vectors, transformed and transfected prokaryotic and eukaryotic host cells, and new and useful methods for cultured growth of such host cells capable of expression of the polypeptide and related products.

Vectors which comprise the isolated nucleic acid molecule described hereinabove also are provided. Suitable vectors comprise, but are not limited to, a plasmid or a virus. These vectors may be transformed into a suitable host cell to form a host cell expression system for the production of a polypeptide having the biological activity of the polypeptide. Suitable host cells include, for example, neuronal cells such as the glial cell line C6, a Xenopus cell such as an oocyte or melanophore cell, as well as numerous mammalian cells and non-neuronal cells.

This invention provides a baculovirus designated Bac-BO45 (ATCC Accession No. VR-2574) which comprises the regulatory elements necessary for expression of DNA in an insect cell operatively linked to DNA encoding the polypeptide so as to permit expression thereof.

This baculovirus (Bac-BO45) was deposited on May 15, 1997, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. VR-2574.

This invention provides a plasmid designated BO-25 (ATCC Accession No. 209036) which comprises the regulatory elements necessary for expression of DNA in a mammalian cell operatively linked to DNA encoding the polypeptide so as to permit expression thereof.

This plasmid (BO-25) was deposited on May 15, 1997, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. 209036.

This invention further provides for any vector or plasmid which comprises modified untranslated sequences, which are beneficial for expression in desired host cells or for use in binding or functional assays. For example, a vector or plasmid with untranslated sequences of varying lengths may express differing amounts of the polypeptide depending upon the host cell used. In an embodiment, the vector or plasmid comprises the coding sequence of the polypeptide and the regulatory elements necessary for expression in the host cell.

This invention provides a cell comprising the above-described plasmid or vector. In an embodiment, the cell is a non-mammalian cell. In a further embodiment, the non-mammalian cell is a Xenopus oocyte cell or a Xenopus melanophore cell.

This invention is directed to a cell comprising the vector of this invention.

In one embodiment, the cell is a non-mammalian cell.

In one embodiment, the non-mammalian cell is a Xenopus oocyte cell or a Xenopus melanophore cell.

In another embodiment, the cell is a mammalian cell.

In another embodiment, the mammalian cell is a COS-7 cell, a 293 human embryonic kidney cell, an NIH-3T3 cell, an LM(tk−) cell or a CHO cell.

This invention is directed to a insect cell comprising the vector of this invention.

In one embodiment, the insect cell is an Sf9 cell, an Sf21 cell or a HighFive cell.

This invention is directed to a cell comprising the vector of this invention.

In one embodiment, the cell is a non-mammalian cell.

In another embodiment, the non-mammalian cell is a

Xenopus oocyte cell or a Xenopus melanophore cell.

In another embodiment, the cell is a mammalian cell.

In another embodiment, the mammalian cell is a COS-7 cell, a 293 human embryonic kidney cell, an NIH-3T3 cell, an LM(tk−) cell or a CHO cell.

This invention is directed to an insect cell comprising the vector of this invention.

In one embodiment, the insect cell is an Sf9 cell, an Sf21 cell or a HighFive cell.

This invention is directed to a membrane preparation isolated from the cell this invention.

In one embodiment, the membrane preparation is isolated from the cell of this invention.

This invention is directed to a nucleic acid probe comprising at least 15 nucleotides, which probe has a unique sequence corresponding to a sequence present within (a) the nucleic acid sequence from nucleotide number 2395 through nucleotide number 2412 of FIG. 4 (Seq. I.D. No. 9) or (b) a reverse complement thereof.

In one embodiment, the nucleotides are deoxyribonucleotides.

In another embodiment, the nucleotides are ribonucleotides.

As used herein, the phrase "specifically hybridizing" means the ability of a nucleic acid molecule to recognize a nucleic acid sequence complementary to its own and to form double-helical segments through hydrogen bonding between complementary base pairs.

Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes the polypeptide into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the DNA molecule which encodes the polypeptide downstream of a bacteriophage promoter such as T3, T7 or SP6. Large amounts of RNA probe may be produced by incubating the labeled nucleotides with the linearized fragment where it contains an upstream promoter in the presence of the appropriate RNA polymerase.

This invention is directed to an antisense oligonucleotide having a unique sequence corresponding to a sequence present within (a) the nucleic acid sequence from nucleotide number 2395 through nucleotide number 2412 of FIG. 4 (Seq. I.D. No. 9) or (b) a reverse complement thereof.

In another embodiment, the nucleic acid is DNA. In another embodiment, the DNA is cDNA. In another embodiment, the DNA is genomic DNA. In another embodiment, the nucleic acid is RNA. In another embodiment, the nucleic acid is linked to a nucleic acid encoding a FLAG® epitope.

In another embodiment, the antisense oligonucleotide is capable of specifically hybridizing to genomic DNA.

In another embodiment, the antisense oligonucleotide comprises chemically modified nucleotides or nucleotide analogues.

This invention is directed to an antibody capable of specifically binding to the polypeptide containing at least a unique sequence corresponding to a sequence present within the amino acid sequence from amino acid number 799 through amino acid number 804 of FIG. 5 (Seq. I.D. No. 10).

In one embodiment, the antibody is capable of competitively inhibiting the binding of the antibody of claim 56 to the polypeptide to which it specifically binds.

In another embodiment, the antibody is a monoclonal antibody.

This invention is directed to a pharmaceutical composition comprising an amount of the oligonucleotide of this invention effective to reduce expression of a polypeptide and a pharmaceutically acceptable carrier.

In one embodiment, the oligonucleotide is coupled to a substance which inactivates mRNA.

In one embodiment, the substance which inactivates mRNA is a ribozyme.

In one embodiment, the pharmaceutically acceptable carrier comprises a structure which binds to a receptor on a cell capable of being taken up by the cells after binding to the structure.

In another embodiment, wherein the pharmaceutically acceptable carrier is capable of binding to a receptor which is specific for a selected cell type.

This invention is directed to a pharmaceutical composition which comprises an amount of the antibody of this invention effective to block binding of a ligand to the polypeptide and a pharmaceutically acceptable carrier.

This invention provides a pharmaceutical composition comprising an amount of a compound effective to increase the activity of leptin and a pharmaceutically acceptable carrier. Included in this invention are pharmaceutically acceptable salts and complexes of all of the polypeptides and compounds described herein.

This invention provides the above-described pharmaceutical composition which comprises an amount of the antibody effective to block binding of a ligand to the above-described polypeptides and a pharmaceutically acceptable carrier.

In the practice of this invention the "pharmaceutically acceptable carrier" is any physiological carrier known to those of ordinary skill in the art useful in formulating pharmaceutical compositions. Examples include, but are not limited to, phosphate buffered saline, physiological saline, water and emulsions, such as oil/water emulsions.

In one embodiment the pharmaceutical carrier may be a liquid and the pharmaceutical composition would be in the form of a solution. In another embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile njectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

In the subject invention a "therapeutically effective amount" is any amount of a compound which, when administered to a subject suffering from a disease against which the compounds are effective, causes reduction, remission, or regression of the disease. In one embodiment the therapeutically effective amount is an amount from about 0.01 mg per subject per day to about 500 mg per subject per day, preferably from about 0.1 mg per subject per day to about 60 mg per subject per day and most preferably from about 1 mg per subject per day to about 20 mg per subject per day.

This invention is directed to a transgenic nonhuman mammal expressing a nucleic acid of this invention.

This invention is directed to a transgenic nonhuman mammal comprising a homologous recombination knockout of a polypeptide expressed by a nucleic acid of this invention.

This invention is directed to a transgenic nonhuman mammal whose genome comprises antisense DNA complementary to a nucleic acid of this invention so placed as to be transcribed into antisense mRNA which is complementary to mRNA encoding a polypeptide and which hybridizes to mRNA encoding a polypeptide, thereby reducing its translation.

In one embodiment, the nucleic acid additionally comprises an inducible promoter.

In another embodiment, the nucleic acid additionally comprises tissue specific regulatory elements.

In another embodiment, the transgenic nonhuman mammal is a mouse.

Animal model systems which elucidate the physiological and behavioral roles of the above-described polypeptides are produced by creating transgenic animals in which the activity of the polypeptide is either increased or decreased, or the amino acid sequence of the expressed polypeptide is altered, by a variety of techniques. Examples of these techniques include, but are not limited to: 1) Insertion of normal or mutant versions of DNA encoding the polypeptide, by microinjection, electroporation, retroviral transfection or other means well known to those skilled in the art, into appropriate fertilized embryos in order to produce a transgenic animal or 2) Homologous recombination of mutant or normal, human or animal versions of these genes with the native gene locus in transgenic animals to alter the regulation of expression or the structure of these polypeptide sequences. The technique of homologous recombination is well known in the art. It replaces the native gene with the inserted gene and so is useful for producing an animal that cannot express native polypeptide but does express, for example, an inserted mutant polypeptide, which has replaced the native polypeptide in the animal's genome by recombination, resulting in underexpression of the polypeptide. Microinjection adds genes to the genome, but does not remove them, and so is useful for producing an animal which expresses its own and added polypeptides, resulting in overexpression of the polypeptides.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a polypeptide is purified from a vector by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

This invention is directed to a process for identifying a chemical compound which specifically binds to a polypeptide of this invention, which comprises contacting the polypeptide with the compound under conditions suitable for binding, and detecting specific binding of the chemical compound to the polypeptide.

In one embodiment, the specific binding of the compound to the polypeptide is detected by means of an antibody which binds to the polypeptide.

In another embodiment, the specific binding of the compound to the polypeptide is detected by a scintillation proximity assay.

In another embodiment, the polypeptide has substantially the same amino acid sequence as that shown in FIG. 5.

In another embodiment, the compound is not previously known to bind to the polypeptide.

In another embodiment, the compound is determined by the process described above.

This invention is directed to a pharmaceutical composition which comprises an effective amount of a compound determined by the above-described process and a pharmaceutically acceptable carrier.

This invention is directed to a process involving competitive binding for identifying a chemical compound which specifically binds to a polypeptide of this invention which comprises separately contacting the polypeptide, with both the chemical compound and a second chemical compound known to bind to the polypeptide, and with only the second chemical compound, under conditions suitable for binding of both compounds, and detecting specific binding of the chemical compound to the polypeptide, a decrease in the binding of the second chemical compound to the polypeptide in the presence of the chemical compound indicating that the chemical compound binds to the polypeptide.

This invention is directed to a process of this invention, wherein the specific binding of the compound to the polypeptide is detected by means of an antibody which binds to the polypeptide.

In one embodiment, the specific binding of the compound to the polypeptide is detected by a scintillation proximity assay.

In another embodiment, the polypeptide has substantially the same amino acid sequence as that shown in FIG. 5.

In another embodiment, the compound is not previously known to bind to the polypeptide.

This invention is directed to a compound determined by the above-described process.

This invention is directed to a pharmaceutical composition which comprises an effective amount of a compound determined by the above-described process and a pharmaceutically acceptable carrier.

This invention is directed to a process for identifying a chemical compound which specifically binds to a polypeptide encoded by a nucleic acid of this invention, which comprises contacting cells containing DNA encoding and expressing on the cell surface the polypeptide, with the compound under conditions suitable for binding, and detecting specific binding of the chemical compound to the polypeptide.

In one embodiment, wherein the polypeptide has substantially the same amino acid sequence as that shown in FIG. 5.

In another embodiment, the compound is not previously known to bind to the polypeptide.

In another embodiment, the compound is determined by the above-described process.

In another embodiment, the pharmaceutical composition which comprises an effective amount of a compound determined by the above-described process and a pharmaceutically acceptable carrier.

In another embodiment, wherein the cell is an insect cell.

In another embodiment, the cell is a mammalian cell.

In another embodiment, the cell is nonneuronal in origin.

In another embodiment, the nonneuronal cell is a COS-7 cell, a 293 human embryonic kidney cell, an NIH-3T3 cell or an LM(tk−) cell.

This invention is directed to a process for identifying a chemical compound which specifically binds to a polypeptide encoded by a nucleic acid of this invention, which comprises contacting a membrane fraction from a cell extract of cells containing DNA encoding and expressing on their cell surface the polypeptide, with the compound under conditions suitable for binding, and detecting specific binding of the chemical compound to the polypeptide.

In one embodiment, the polypeptide has substantially the same amino acid sequence as that shown in FIG. 5.

In another embodiment, the compound is not previously known to bind to the polypeptide.

In another embodiment, the compound is determined by the above-described process.

This invention is directed to a pharmaceutical composition which comprises an effective amount of a compound determined by the above-described process and a pharmaceutically acceptable carrier.

In one embodiment, the cell is an insect cell.

In another embodiment, the cell is a mammalian cell.

In another embodiment, the cell is nonneuronal in origin.

In another embodiment, the nonneuronal cell is a COS-7 cell, a 293 human embryonic kidney cell, an NIH-3T3 cell or an LM(tk−) cell.

This invention is directed to a process involving competitive binding for identifying a chemical compound which specifically binds to a polypeptide encoded by a nucleic acid of this invention, which comprises separately contacting cells expressing on their cell surface the polypeptide, with both the chemical compound and a second chemical compound known to bind to the polypeptide, and with only the second chemical compound, under conditions suitable for binding of both compounds, and detecting specific binding of the chemical compound to the polypeptide, a decrease in the binding of the second chemical compound to the polypeptide in the presence of the chemical compound indicating that the chemical compound binds to the polypeptide.

In one embodiment, the polypeptide has the amino ac d sequence shown in FIG. 5 (Seq. I.D. No. 10).

In another embodiment, the cell is an insect cell.

In another embodiment, the cell is a mammalian cell.

In another embodiment, the cell is nonneuronal in origin.

In another embodiment, the nonneuronal cell is a COS-7 cell, a 293 human embryonic kidney cell, an NIH-3T3 cell or an LM(tk−) cell.

In another embodiment, the compound is not previously known to bind to the polypeptide.

This invention is directed to a compound determined by the above-described process.

This invention is directed to a pharmaceutical composition which comprises an effective amount of a compound determined by the above-described process and a pharmaceutically acceptable carrier.

This invention is directed to a process involving competitive binding for identifying a chemical compound which specifically binds to a polypeptide encoded by a nucleic acid of this invention, which comprises separately contacting a membrane fraction from a cell extract of cells expressing on their cell surface the polypeptide, with both the chemical compound and a second chemical compound known to bind to the polypeptide, and with only the second chemical compound, under conditions suitable for binding of both compounds, and detecting specific binding of the chemical compound to the polypeptide, a decrease in the binding of the second chemical compound to the polypeptide in the presence of the chemical compound indicating that the chemical compound binds to the polypeptide.

In one embodiment, the polypeptide has the amino acid sequence shown in FIG. 5 (Seq. I.D. No. 10).

In another embodiment, the cell is an insect cell.

In another embodiment, the cell is a mammalian cell.

In another embodiment, the cell is nonneuronal in origin.

In another embodiment, the nonneuronal cell is a COS-7 cell, a 293 human embryonic kidney cell, an NIH-3T3 cell or an LM(tk−) cell.

In another embodiment, wherein the compound is not previously known to bind to the polypeptide.

This invention is directed to a compound determined by the process of this invention.

This invention is directed to a pharmaceutical composition which comprises an effective amount of a compound determined by the above-described process and a pharmaceutically acceptable carrier.

This invention is directed to a method of screening a plurality of chemical compounds not known to bind to a polypeptide encoded by a nucleic acid of this invention to identify a compound which specifically binds to the polypeptide, which comprises:

(a) contacting cells transfected with and expressing DNA encoding the polypeptide with a compound known to bind specifically to the polypeptide;

(b) contacting the preparation of step (a) with the plurality of compounds not known to bind specifically to the polypeptide, under conditions permitting binding of compounds known to bind the polypeptide;

(c) determining whether the binding of the compound known to bind to the polypeptide is reduced in the presence of the plurality of compounds, relative to the binding of the compound in the absence of the plurality of compounds; and if so (d) separately determining the binding to the polypeptide of each compound included in the plurality of compounds, so as to thereby identify the compound which specifically binds to the polypeptide.

In one embodiment, the cell is a mammalian cell.

In another embodiment, the mammalian cell is non-neuronal in origin.

In another embodiment, the non-neuronal cell is a COS-7 cell, a 293 human embryonic kidney cell, an LM(tk−) cell or an NIH-3T3 cell.

This invention is directed to a pharmaceutical composition comprising an effective amount of a compound identified by the above-described method and a pharmaceutically acceptable carrier.

This invention is directed to a method of screening a plurality of chemical compounds not known to bind to a polypeptide of this invention to identify a compound which specifically binds to the polypeptide, which comprises:

(a) preparing a cell extract or cell supernatant from cells transfected with and expressing DNA encoding the polypeptide and contacting the cell extract or cell supernatant with a compound known to bind specifically to the polypeptide;

(b) contacting the preparation of step (a) with the plurality of compounds not known to bind specifically to the polypeptide, under conditions permitting binding of compounds known to bind the polypeptide;

(c) determining whether the binding of the compound known to bind to the polypeptide is reduced in the presence of the compounds, relative to the binding of the compound in the absence of the plurality of compounds; and if so (d) separately determining the binding to the polypeptide of each compound included in the plurality of compounds, so as to thereby identify the compound which specifically binds to the polypeptide.

In one embodiment, the cell is a mammalian cell.

In another embodiment, the mammalian cell is non-neuronal in origin.

In another embodiment, the non-neuronal cell is a COS-7 cell, a 293 human embryonic kidney cell, an LM(tk−) cell or an NIH-3T3 cell.

This invention is directed to a pharmaceutical composition comprising an effective amount of a compound identified by the above-described method and a pharmaceutically acceptable carrier.

This invention is directed to a process for determining whether a chemical compound is an Ob receptor agonist which comprises contacting cells transfected with and expressing DNA of this invention with the compound under conditions permitting the activation of the Ob receptor, and detecting an increase in Ob receptor activity, so as to thereby determine whether the compound is an Ob receptor agonist.

This invention is directed to a process for determining whether a chemical compound is an Ob receptor agonist which comprises preparing a cell extract from cells transfected with and expressing DNA of this invention, isolating a membrane fraction from the cell extract, contacting the membrane Fraction with the compound under conditions permitting the activation of the Ob receptor, and detecting an increase in Ob receptor activity, so as thereby determine whether the compound is an Ob receptor agonist.

This invention is directed to a process for determining whether a chemical compound is an Ob receptor antagonist which comprises contacting cells transfected with and expressing DNA of this invention with the compound in the presence of a known Ob receptor agonist, under conditions permitting the activation of an Ob receptor, and detecting a decrease in Ob receptor activity, so as to thereby determine whether the compound is an Ob receptor antagonist.

This invention is directed to a process for determining whether a chemical compound is an Ob receptor antagonist which comprises preparing a cell extract from cells transfected with and expressing DNA of this invention, isolating a membrane fraction from the cell extract, contacting the membrane fraction with the ligand in the presence of a known Ob receptor agonist, under conditions permitting the activation of the Ob receptor, and detecting a decrease in Ob receptor activity, so as to thereby determine whether the compound is an Ob receptor antagonist.

In one embodiment, the Ob receptor is a mammalian Ob receptor.

In another embodiment, the cell is an insect cell.

In another embodiment,the cell is a mammalian cell.

In another embodiment, the cell is nonneuronal in origin.

In another embodiment, the nonneuronal cell is a COS-7 cell, a 293 human embryonic kidney cell, an NIH-3T3 cell or an LM(tk−) cell.

This invention is directed to a pharmaceutical composition comprising an effective amount of a polypeptide of this invention and a pharmaceutically acceptable carrier.

In one embodiment, the pharmaceutical composition is a liquid.

In another embodiment, the carrier is isotonic saline.

This invention is directed to a method for determining whether a compound modulates leptin activity which comprises:

(a) administering to an animal a polypeptide of this invention and measuring the amount of food intake, metabolic, or body weight changes in the animal;

(b) administering to a second animal both the polypeptide and the compound, and measuring the amount of food intake, metabolic, or body weight changes in the second animal; and (c) determining whether the amount of food intake, metabolic, or body weight change is altered in the presence of the compound relative to the amount of food intake, metabolic, or body weight change in the absence of the compound, so as to thereby determine whether the compound modulates leptin activity.

This invention is directed to a method of screening a plurality of compounds to identify a compound which modulates leptin activity which comprises:

(a) administering to an animal a polypeptide of this invention and measuring the amount of food intake, metabolic, or body weight changes in the animal;

(b) administering to a second animal the polypeptide and at least one compound of the plurality of compounds and measuring the amount of food intake, metabolic, or body weight changes in the animal;

(c) determining whether the amount of food intake, metabolic, or body weight change is altered in the presence of at least one compound of the plurality relative to the amount of food intake, metabolic, or body weight change in the absence of at least one compound of the plurality, and if so;

(d) separately determining whether each compound modulates leptin activity according to the above-described method, so as to thereby identify a compound which modulates leptin activity.

This invention is directed to a method of treating an abnormality in a subject, wherein the abnormality is alleviated by modulating the activity of leptin in the subject, which comprises administering to a subject an amount of the pharmaceutical composition of this invention effective to modulate the activity of leptin in the subject, thereby treating the abnormality in the subject.

In one embodiment,the pharmaceutical composition is administered with food.

In another embodiment, the subject is a vertebrate, a mammal, a human, a canine or a feline.

In another embodiment, the pharmaceutical composition comprises an injectable carrier.

In another embodiment, the pharmaceutical composition comprises a wild-type polypeptide.

This invention is directed to a method of modulating feeding behavior or metabolism of a subject which comprises administering to the subject an amount of a polypeptide of this invention effective to modulate the feeding behavior or metabolism of the subject so as to thereby modulate feeding behavior or metabolism of the subject.

In one embodiment, the subject's anorexia is treated.

In another embodiment, the subject's weight loss associated with cancer is treated.

In another embodiment, the subject's reduced appetite associated with aging is treated.

In another embodiment, the subject's obesity is treated.

In another embodiment, the subject's bulimia is treated.

In another embodiment, the compound is administered with food.

In another embodiment, the subject is a vertebrate, a mammal, a human, a canine or a feline.

In another embodiment, the polypeptide is administered in a pharmaceutical composition comprising an injectable carrier.

In another embodiment, the polypeptide is a wild-type polypeptide.

This invention is directed to a method of modulating feeding behavior or metabolism of a subject which comprises administering a polypeptide of this invention and a compound which binds to the Y5 receptor, the amount of such polypeptide and compound being effective to modulate the feeding behavior or metabolism of the subject.

In one embodiment, the polypeptide and the compound are administered in combination.

In another embodiment, the polypeptide and the compound are administered separately.

In another embodiment, the polypeptide and the compound are administered once.

In another embodiment, the polypeptide and the compound are administered alternately.

In another embodiment, the polypeptide and the compound are administered repeatedly.

In another embodiment, the polypeptide and compound are administered with food.

In another embodiment, the subject is a vertebrate, a mammal, a human, a canine or a feline.

In another embodiment, the polypeptide and compound are administered in a pharmaceutical composition comprising an injectable carrier.

In another embodiment, the polypeptide is a wild-type polypeptide.

This invention is directed to a method of modulating feeding behavior or metabolism in a subject which comprises administering to the subject an amount of a compound which binds to a polypeptide of the invention effective to alter the activity of leptin in the subject, so as to thereby modulate feeding behavior or metabolism of the subject.

In one embodiment, the subject's anorexia is treated.

In another embodiment, the subject's weight loss associated with cancer is treated.

In another embodiment, the subject's reduced appetite associated with aging is treated.

In another embodiment, the subject's obesity is treated.

In another embodiment, the subject's bulimia is treated.

In another embodiment, the compound is administered with food.

In another embodiment, the subject is a vertebrate, a mammal, a human, a canine or a feline.

In another embodiment, the compound is administered in a pharmaceutical composition comprising an injectable carrier.

In another embodiment, the polypeptide is a wild-type polypeptide.

This invention is directed to a method of modulating feeding behavior or metabolism of a subject which comprises administering a compound which binds to a polypeptide of the invention and a second compound which binds to the Y5 receptor, the amount of the first compound and the second compound being effective to modulate the feeding behavior or metabolism of the subject.

In one embodiment, the compound and the second compound are administered in combination.

In another embodiment, the compound and the second compound are administered separately.

In another embodiment, the compound and the second compound are administered once.

In another embodiment, the compound and the second compound are administered alternately.

In another embodiment, the compound and the second compound are administered repeatedly.

In another embodiment, the compound and second compound are administered with food.

In another embodiment, the subject is a vertebrate, a mammal, a human, a canine or a feline.

In another embodiment, the compound and second compound are administered in a pharmaceutical composition comprising an injectable carrier.

In another embodiment, the polypeptide is a wild-type polypeptide.

This invention is directed to a method of detecting expression of a polypeptide of this invention by detecting the presence of mRNA coding for the polypeptide which comprises obtaining total mRNA from the cell and contacting the mRNA so obtained with the nucleic acid probe of this invention under hybridizing conditions, detecting the presence of mRNA hybridized to the probe, and thereby detecting the expression of the polypeptide by the cell.

This invention is directed to a method of detecting the presence of a polypeptide which comprises contacting the cell or cell supernatant with the antibody of this invention under conditions permitting binding of the antibody to the polypeptide, detecting the presence of the antibody bound to the cell or cell supernatant, and thereby detecting the presence of a polypeptide.

This invention is directed to a method of determining the physiological effects of varying levels of activity of polypeptides which comprises producing a transgenic nonhuman mammal of this invention whose levels of polypeptide activity are varied by use of an inducible promoter which regulates polypeptide expression.

This invention is directed to a method of determining the physiological effects of varying levels of activity of polypeptides which comprises producing a panel of transgenic nonhuman mammals of this invention each expressing a different amount of polypeptide.

This invention is directed to a method for diagnosing a predisposition to a disorder associated with the activity of a specific polypeptide allele which comprises:

(a) obtaining DNA of subjects suffering from the disorder;

(b) performing a restriction digest of the DNA with a panel of restriction enzymes;

(c) electrophoretically separating the resulting DNA fragments on a sizing gel;

(d) contacting the resulting gel with a nucleic acid probe capable of specifically hybridizing with a unique sequence included within the sequence of a nucleic acid molecule encoding a polypeptide and labeled with a detectable marker;

(e) detecting labeled bands which have hybridized to the nucleic acid of this invention labeled with a detectable marker to create a unique band pattern specific to the DNA of subjects suffering from the disorder;

(f) preparing DNA obtained for diagnosis by steps a–e; and (g) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

In one embodiment, the disorder associated with the activity of a specific polypeptide allele is diagnosed.

This invention is directed to a method of preparing the purified polypeptide this invention which comprises:

(a) inducing cells to express the polypeptide;

(b) recovering the polypeptide from the induced cells; and (c) purifying the polypeptide so recovered.

In one embodiment, the cell is placed in a serum-free growth medium.

In another embodiment, the polypeptide is recovered by affinity chromatography.

In another embodiment, the affinity chromatography comprises the use of leptin.

In another embodiment, the polypeptide is recovered by means of antibody binding.

In another embodiment, the antibody is directed to a flag epitope modification of the wild-type polypeptide.

This invention is directed to a method of preparing the purified polypeptide of this invention which comprises:

(a) inserting nucleic acid encoding the polypeptide in a suitable vector;

(b) introducing the resulting vector in a suitable host cell;

(c) placing the resulting cell in suitable condition permitting the production of the isolated polypeptide;

(d) recovering the polypeptide produced by the resulting cell; and (e) purifying the polypeptide so recovered.

In one embodiment, the cell is placed in a serum-free growth medium.

In another embodiment, the polypeptide is recovered by affinity chromatography.

In another embodiment, the affinity chromatography comprises the use of leptin.

In another embodiment, the polypeptide is recovered by means of antibody binding.

In another embodiment, the antibody is directed to a flag epitope modification of the wild-type polypeptide.

This invention will be better understood from the Experimental Details which follow. However, one skilled in the art will readily appreciate that the specific methods and results discussed are merely illustrative of the invention as described more fully in the claims which follow thereafter.

Experimental Details

Materials and Methods

Cloning and Sequencing a Novel Human Ob-Re Receptor

3' RACE of Human RNAs for hOb-Re

3' RACE (rapid analysis of cDNA ends) was performed on human kidney, liver, skeletal muscle, heart, adipose and lung RNAs using a Marathon cDNA Amplification Kit (Clontech). Total RNA was prepared from human adipose tissue using RNAgents Total RNA Isolation System (Promega). For other tissues, total RNA was purchased from Clontech. All total RNAs were poly A+ selected using a FastTrack mRNA Isolation Kit (Invitrogen Corp., San Diego, Calif.). For 3' RACE, double stranded (ds) cDNA synthesis, adaptor ligation and nested PCR were performed according to the Marathon cDNA Amplification protocol. The initial PCR reaction was performed on 1 $\mu$L of a 50 fold dilution of the ligated cDNA using the supplier's Adaptor Primer 1 (AP1) and one of the following gene-specific primers (GSP): DC17, BB75 or BB76. One $\mu$L of this initial PCR reaction was re-amplified using Adaptor Primer 2 (AP2) and one of the following GSPs: DC18, DC4, BB76 or BB87. PCR was carried out using an Advantage KlenTaq Polymerase Kit (Clontech) under the following conditions: 30 sec at 94° C., 4 min at 72° C. for 5 cycles, 30 sec at 94° C., 4 min at 70° C. for 5 cycles, 20 sec at 94° C., 4 min at 68° C. for 25 cycles (for first PCR) or 18 cycles (for nested PCR), with a pre- and post-incubation of 1 min at 94° C. and 7 min at 68° C., respectively. Bands from the nested PCR were isolated from TAE gels using a GENECLEAN III kit (BIO 101, Vista, Calif.) and sequenced using AmpliTaq DNA Polymerase, FS (Perkin Elmer). The sequences were run on an ABI PRISM 377 DNA Sequencer and analyzed using the Wisconsin Package (GCG, Genetics Computer Group, Madison, Wis.).

Low Stringency PCR for hOb-Re

PCR was performed on cDNAs from human kidney, liver, skeletal muscle and heart using a forward primer from hOb-Rb (DC4) and a reverse primer from the mouse Ob-Re sequence (BB116). PCR was carried out using both the Expand Long Template PCR System and the Expand High Fidelity System (Boehringer Mannheim) under the following conditions: 1 min at 94° C., 2 min at 42° C., 4 min at 68° C. for 36 cycles, with a pre- and post-incubation of 4 min at 94° C. and 10 min at 68° C., respectively.

Identification of Human Ob-Re-Specific Sequence

Mouse genomic DNA (100 ng, Clontech) was amplified using forward (BB130) and reverse (BB131) PCR primers from mouse Ob-Rb. Human genomic DNA (100 ng, Clontech) was amplified using forward (DC4) and reverse (BB132) PCR primers from human Ob-Rb. PCR was carried out using the Expand Long Template PCR System (Boehringer Mannheim) under the following conditions: 1 min at 92° C., 2 min at 60° C., 10 min at 68° C. for 30 cycles, with a pre- and post-incubation of 4 min at 92° C. and 10 min at 68° C., respectively. A 9.5 kb band from mouse and a 2.2 kb band from human were isolated from a 1% TAE gel using a GENECLEAN III kit (BIO 101, Vista, Calif.) and sequenced using AmpliTaq DNA Polymerase, FS (Perkin Elmer). The sequence was run on an ABI PRISM 377 DNA Sequencer and analyzed using the Wisconsin Package (GCG, Genetics Computer Group, Madison, Wis.). The sequence of this piece was identical to the human Ob-Rb receptor from primer DC4 up to nucleotide 2495, after which it diverged completely from any of the published human Ob receptors. This novel sequence contained an open reading frame encoding 6 amino acids, and shares 83% nucleotide identity to the mouse Ob-Re.

Localization of Ob-Re in Human Tissues

RT-PCR was used to identify human tissues that express hOb-Re, using the forward primer DC4 and a reverse primer from hOb-Re, BB138. PCR was carried out using the Expand Long Template PCR System (Boehringer Mannheim) under the following conditions: 1 min at 94° C., 2 min at 62° C., 2 min at 68° C. for 30 cycles, with a pre- and post-incubation of 5 min at 94° C. and 10 min at 68° C., respectively. The templates used were cDNA from hypothalamus, total brain, heart, kidney, skeletal muscle, liver, lung and adipose as well as RACE reactions from heart, skeletal muscle, adipose and lung which had been amplified previously with primers DC17 and AP1 (see above). A 0.2 kb band was amplified from the lung RACE product. To verify that this 0.2 kb product from lung was derived from mRNA and was not a genomic DNA contamination, we amplified human lung cDNA with a forward PCR primer from hOb-Rb (DC16) and a reverse primer from hOb-Re (BB139) and then reamplified one $\mu$L of this product with primers DC16 and BB138. A 2 kb and a 0.26 kb band were isolated from a 1% TAE gel using a GENECLEAN III kit (BIO 101, Vista, Calif.) and partially sequenced using AmpliTaq DNA Polymerase, FS (Perkin Elmer). The sequence was run on an ABI PRISM 377 DNA Sequencer and analyzed using the Wisconsin Package (GCG, Genetics Computer Group, Madison, Wis.). The 2 kb band contained an intron while the 0.26 kb band contained the sequence for the 3' end of the hOb-Re receptor. In contrast, when DC16 and BB138 were used to amplify human genomic DNA, only a 2 kb band was isolated.

Preparation of Full-length hOb-Re Construct

A 2.4 kb ClaI-EarI fragment encoding nucleotides 1 to 2371 of hOb-Rb, was isolated from a hOb-Rb construct in the vector pEXJ. Two overlapping oligonucleotides (BB157 and BB158) were synthesized, corresponding to nucleotides 2372 to 2395 of hOb-Rb and nucleotides 2396–2415 of hOb-Re, and incorporating a digested EarI site at the 5' end and a digested HindIII site at the 3' end. A full-length hOb-Re construct, designated BO25, was obtained by ligating the ClaI-EarI fragment and the oligonucleotide to the vector pEXJ cut with ClaI and HindIII and has been deposited with the ATCC (ATCC Accession No. 209036).

Transient Transfection in COS-7 Cells

COS-7 cells are grown on 150 mm plates in DMEM with supplements (Dulbecco's Modified Eagle Medium with 10% bovine calf serum, 4 mM glutamine, 100 units/mL penicillin, 100 $\mu$g/mL streptomycin) at 37° C., 5% $CO_2$. Stock plates of COS-7 cells are trypsinized and split 1:6 every 3–4 days. hOb-Re (BO25) was transiently transfected into COS-7 cells by the DEAE dextran method, using 20 $\mu$g DNA/T150 flask (Cullen, 1987). Transfected cells were plated in 96-well plates in 100 ul medium.

Scintillation Proximity Assay 100 ul of binding buffer (composition: $CaCl_2$, 1.2 mM; Hepes, 20 mM; NaCl, 9.9 mM; KCl 5.4 mM; $KH_2PO_4$, 0.44 mM; $MgSO_4$, 0.81 mM) containing 0.1 nM [$^{125}$I] leptin and 1.0% BSA were added to each well of a 96-well plate containing hOb-Re-transfected COS-7 cells. Finally, 50 $\mu$l of SPA beads (Amersham International, England; 20 mg/mL in binding buffer) were added to each well and the cells were incubated for 24 hrs at room temperature on a shaking rotor. 200 $\mu$L aliquots were removed from each well and counted in scintillation counter at 80% efficiency. Other cells expressing hOb-Re and supernatant (e.g., culture medium) from such cells may also be used for binding assays, such as insect cells and their supernatants, amphibian cells or other mammalian cells described herein.

Competitive binding assays may be performed similarly, wherein the displacement of [$^{125}$I] leptin by a test compound is evaluated by separately measuring the binding of [$^{125}$I] leptin in the presence of, and in the absence of, the test compound. Multiple concentrations of test compound may be also be used, to determine the $IC_{50}$ of the compound with respect to leptin (or other ligands known to bind to Ob receptors) according to methods well known in the art. In addition, determination of the $K_d$ of leptin for hOb-Re may also be accomplished using SPA detection, such that Ki's may be calculated using the method of Cheng and Prusoff (1973). Additional methods of detecting specific binding include using gel filtration, affinity columns, or radioimmunoassay utilizing an antibody to the receptor.

Production of Recombinant Baculovirus

Recombinant baculovirus expressing hOb-Re was generated using the Bac-to-Bac Baculovirus Expression System (Gibco BRL). A SacI/HindIII fragment containing the entire encoding region of hOb-Re was isolated from BO25, and ligated to the vector pFASTBacI at the SacI and HindIII sites. A second construct was made, using a Chameleon Double-Stranded Site-Directed Mutagenesis Kit (Stratagene), which differed in that it contained an 8 amino acid FLAG® epitope (Kodak) downstream of the signal sequence cleavage site in hOB-Re. Recombinant bacmid *E. coli* colonies were generated and DNA for each was isolated as described by the manufacturer. The constructs with and without the FLAG® epitope are designated BO47 and BO45, respectively.

Transfection of Recombinant Bacmid DNA into SF21 Cells

SF21 cells (Invitrogen) are grown in T75 flasks in TMN-FH Insect Medium (PharMingen) at 27° C. without $CO_2$ supplementation. Stock plates of SF21 cells are gently dislodged under a stream of media and split 1:4 every 2–3 days. SF21 cells grown in 6-well plates were transfected with recombinant bacmid DNA, BO45 or BO47, using CellFECTIN Reagent (Gibco BRL) as described by the manufacturer. Virus-containing supernatants were collected 96 and 144 hours after transfection.

Amplification of Viral Stock

SF21 cells grown in 6-well plates were infected with the viral supernatant from the BO45-transfected cells above at 1, $10^{-1}$, $10^{-2}$, $10^{-3}$, $10^{-4}$ and $10^{-5}$ dilutions. Supernatants from these were collected 120 hours after infection. To determine the viral titer of the amplified stock, a viral plaque assay was performed on supernatant from the $10^{-1}$ dilution-infected cells, designated P3-$10^{-1}$, according to protocol for BaculoGold Baculovirus kit (PharMingen). 500 mL of high-titer viral stock was generated by infecting SF21 cells in T150 flasks with the supernatant from P3-$10^{-1}$ at a multiplicity of infection (MOI) of 0.1 and collecting supernatant 120 hours after infection. This supernatant was designated Bac-BO45 and deposited with the ATCC (ATCC Accession No. VR-2574). To optimize the MOI and the time course for leptin binding studies, SF21 cells in 6-well were infected with the supernatant from P3-$10^{-1}$ at MOIs of 1, 2, 5 and 10 and supernatant collected at 48, 72, 96 and 120 hours.

Cell Culture

In addition to the COS-7 cells described above, other cells may be transfected with the hOb-Re receptor using standard methods.

Human embryonic kidney 293 cells are grown on 150 mm plates in D-MEM with supplements (minimal essential medium) with Hanks' salts and supplements (Dulbecco's Modified Eagle Medium with 10% bovine calf serum, 4 mM glutamine, 100 units/mL penicillin/100 $\mu$g/mL streptomycin) at 37° C., 5% $CO_2$. Stock plates of 293 cells are trypsinized and split 1:6 every 3–4 days. Mouse fibroblast LM(tk−) cells are grown on 150 mm plates in D-MEM with supplements (Dulbecco's Modified Eagle Medium with 10% bovine calf serum, 4 mM glutamine, 100 units/mL penicillin/100 $\mu$g/mL streptomycin) at 37° C., 5% $CO_2$. Stock plates of LM(tk−) cells are trypsinized and split 1:10 every 3–4 days.

LM(tk−) cells stably transfected with the human Ob-Re receptor may be routinely converted from an adherent monolayer to a viable suspension. Adherent cells are harvested with trypsin at the point of confluence, resuspended in a minimal volume of complete DMEM for a cell count, and further diluted to a concentration of $10^6$ cells/mL in suspension media (10% bovine calf serum, 10% 10× Medium 199 (Gibco), 9 mM $NaHCO_3$, 25 mM glucose, 2 mM L-glutamine, 100 units/mL penicillin/100 $\mu$g/mL streptomycin, and 0.05% methyl cellulose). Cell suspensions are maintained in a shaking incubator at 37° C., 5% $CO_2$ for 24 hours. Membranes harvested from cells grown in this manner may be stored as large, uniform batches in liquid nitrogen. Alternatively, cells may be returned to adherent cell culture in complete DMEM by distribution into 96-well microtiter plates coated with poly-D-lysine (0.01 mg/mL) followed by incubation at 37° C., 5% $CO_2$ for 24 hours.

Mouse embryonic fibroblast NIH-3T3 cells are grown on 150 mm plates in Dulbecco's Modified Eagle Medium (DMEM) with supplements (10% bovine calf serum, 4 mM glutamine, 100 units/mL penicillin/100 $\mu$g/mL streptomycin) at 37° C., 5% CO2. Stock plates of NIH-3T3 cells are trypsinized and split 1:15 every 3–4 days. Chinese hamster ovary (CHO) cells are grown on 150 mm plates in HAM's F-12 medium with supplements (10% bovine calf serum, 4 mM L-glutamine and 100 units/mL penicillin/100 ug/mL streptomycin) at 37° C., 5% CO2. Stock plates of CHO cells are trypsinized and split 1:8 every 3–4 days.

Sf9 and Sf21 cells are grown in monolayers on 150 mm tissue culture dishes in TMN-FH media supplemented with 10% fetal calf serum, at 27° C., no $CO_2$. High Five insect cells are grown on 150 mm tissue culture dishes in Ex-Cell 400™ medium supplemented with L-Glutamine, also at 27° C., no $CO_2$.

Transfection

The receptors described herein may be transiently transfected into COS-7 cells by the DEAE-dextran method, using 1 $\mu$g of DNA/$10^6$ cells (Cullen, 1987). In addition, Schneider 2 Drosophila cells may be cotransfected with vectors containing the receptor gene, under control of a promoter which is active in insect cells, and a selectable resistance gene, eg., the G418 resistant neomycin gene, for expression of the human Ob-Re receptor.

Stable Transfection

The human Ob-Re receptor may be co-transfected with a G-418 resistant gene into the human embryonic kidney 293 cell line by a calcium phosphate transfection method (Cullen, 1987). Stably transfected cells are selected with G-418. Human Ob-Re receptors may be similarly transfected into mouse fibroblast LM(tk−) cells, Chinese hamster ovary (CHO) cells and NIH-3T3 cells, or other suitable host cells.

Membrane Preparations

LM(tk−) cells stably transfected with the DNA encoding the mammalian receptors disclosed herein may be routinely converted from an adherent monolayer to a viable suspension. Adherent cells are harvested with trypsin at the point of confluence, resuspended in a minimal volume of complete DMEM for a cell count, and further diluted to a concentration of $10^6$ cells/ml in suspension media (10% bovine calf serum, 10% 10× Medium 199 (Gibco), 9 mM $NaHCO_3$, 25 mM glucose, 2 mM L-glutamine, 100 units/ml penicillin/100 $\mu$g/ml streptomycin, and 0.05% methyl cellulose). Cell suspensions are maintained in a shaking incubator at 37° C., 5% $CO_2$ for 24 hours. Membranes harvested from cells grown in this manner may be stored as large, uniform batches in liquid nitrogen. Alternatively, cells may be returned to adherent cell culture in complete DMEM by distribution into 96-well microtiter plates coated with poly-D-lysine (0.01 mg/ml) followed by incubation at 37° C., 5% $CO_2$ for 24 hours.

Radioligand Binding Assays

Transfected cells from culture flasks are scraped into 5 ml of Tris-HCl, 5mM EDTA, pH 7.5, and lysed by sonication. The cell lysates are centrifuged at 1000 rpm for 5 min. at 4° C., and the supernatant is centrifuged at 30,000×g for 20 min. at 4° C. The pellet is suspended in binding buffer (50 mM Tris-HCl, 5 mM $MgSO_4$, 1 mM EDTA at pH 7.5 supplemented with 0.1% BSA, 2 μg/ml aprotinin, 0.5 mg/ml leupeptin, and 10 μg/ml phosphoramidon). Optimal membrane suspension dilutions, defined as the protein concentration required to bind less than 10% of the added radioligand, are added to 96-well polpropylene microtiter plates containing $^3$H-labeled compound, unlabeled compounds, and binding buffer to a final volume of 250 μl. In equilibrium saturation binding assays membrane preparations are incubated in the presence of increasing concentrations of [$^3$H]-labeled compound. The binding affinities of the different compounds are determined in equilibrium competition binding assays, using [$^3$H]-labeled compound in the presence of ten to twelve different concentrations of the displacing ligands. Binding reaction mixtures are incubated for 1 hr at 30° C., and the reaction stopped by filtration through GF/B filters treated with 0.5% polyethyleneimine, using a cell harvester. Radioactivity may be measured by scintillation counting and data are analyzed by a computerized non-linear regression program. Non-specific binding is defined as the amount of radioactivity remaining after incubation of membrane protein in the presence of unlabeled. Protein concentration may be measured by the Bradford method using Bio-Rad Reagent, with bovine serum albumin as a standard.

Functional Assays

Cyclic AMP (cAMP) Formation Assay

The receptor-mediated inhibition of cyclic AMP (cAMP) formation may be assayed in transfected cells expressing the mammalian receptors described herein. Cells are plated in 96-well plates and incubated in Dulbeccos's phosphate buffered saline (PBS) supplemented with 10 mM HEPES, 5 mM theophylline, 2 μg/ml aprotinin, 0.5 mg/ml leupeptin, and 10 μg/ml phosphoramidon for 20 min at 37° C., in 5% $CO_2$. Test compounds are added and incubated for an additional 10 min at 37° C. The medium is then aspirated and the reaction stopped by the addition of 100 mM HCl. The plates are stored at 4° C. for 15 min, and the cAMP content in the stopping solution measured by radioimmunoassay. Radioactivity may be quantified using a gamma counter equipped with data reduction software.

Arachidonic Acid Release Assay

Stably transfected cells with the mammalian receptors described herein are seeded into 96 well plates and grown for 3 days in HAM's F-12 with supplements. $^3$H-arachidonic acid (specific activity=0.75 μCi/ml) is delivered as a 100 μL aliquot to each well and samples were incubated at 37° C., 5% $CO_2$ for 18 hours. The labeled cells are washed three times with 200 μL HAM's F-12. The wells are then filled with medium (200 μL) and the assay is initiated with the addition of peptides or buffer (22 μL). Cells are incubated for 30 min at 37° C., 5% $CO_2$. Supernatants are transferred to a microtiter plate and evaporated to dryness at 75° C. in a vacuum oven. Samples are then dissolved and resuspended in 25 μL distilled water. Scintillant (300 μL) is added to each well and samples are counted for $^3$H in a Trilux plate reader. Data are analyzed using nonlinear regression and statistical techniques available in the GraphPAD Prism package (San Diego, Calif.).

Intracellular Calcium Mobilization Assay

The intracellular free calcium concentration may be measured by microspectroflourometry using the fluorescent indicator dye Fura-2/AM (Bush et al, 1991). Stably transfected cells are seeded onto a 35 mm culture dish containing a glass coverslip insert. Cells are washed with HBS and loaded with 100 μL of Fura-2/AM (10 μM) for 20 to 40 min. After washing with HBS to remove the Fura-2/AM solution, cells are equilibrated in HBS for 10 to 20 min. Cells are then visualized under the 40× objective of a Leitz Fluovert FS microscope and fluorescence emission is determined at 510 nM with excitation wavelengths alternating between 340 nM and 380 nM. Raw fluorescence data are converted to calcium concentrations using standard calcium concentration curves and software analysis techniques.

Phosphoinositide Metabolism Assay

Cells stably expressing the mammalian receptor cDNA described herein are plated in 96-well plates and grown to confluence. The day before the assay the growth medium is changed to 100 μl of medium containing 1% serum and 0.5 μCi [$^3$H]myo-inositol, and the plates are incubated overnight in a $CO_2$ incubator (5% $CO_2$ at 37° C.). Alternatively, arachidonic acid release may be measured if [$^3$H] arachidonic acid is substituted for the [$^3$H]myo-inositol. Immediately before the assay, the medium is removed and replaced by 200 μL of PBS containing 10 mM LiCl, and the cells are equilibrated with the new medium for 20 min. During this interval cells are also equilibrated with the antagonist, added as a 10 μL aliquot of a 20-fold concentrated solution in PBS. The [$^3$H]inositol-phosphates accumulation from inositol phospholipid metabolism may be started by adding 10 μL of a solution containing the agonist. To the first well 10 μL may be added to measure basal accumulation, and 11 different concentrations of agonist are assayed in the following 11 wells of each plate row. All assays are performed in duplicate by repeating the same additions in two consecutive plate rows. The plates are incubated in a $CO_2$ incubator for 1 hr. The reaction may be terminated by adding 15 μL of 50% v/v trichloroacetic acid (TCA), followed by a 40 min. incubation at 4° C. After neutralizing TCA with 40 μL of 1 M Tris, the content of the wells may be transferred to a Multiscreen HV filter plate (Millipore) containing Dowex AG1-X8 (200–400 mesh, formate form). The filter plates are prepared adding 200 μL of Dowex AG1-X8 suspension (50% v/v, water: resin) to each well. The filter plates are placed on a vacuum manifold to wash or elute the resin bed. Each well is washed 2 times with 200 μL of water, followed by 2×200 μL of 5 mM sodium tetraborate/60 mM ammonium formate. The [$^3$H] IPs are eluted into empty 96-well plates with 200 μL of 1.2 M ammonium formate/0.1 formic acid. The content of the wells is added to 3 ml of scintillation cocktail, and the radioactivity is determined by liquid scintillation counting.

GTPγS Functional Assay

Membranes from cells transfected with the mammalian receptors described herein are suspended in assay buffer (50 mM Tris, 100 mM NaCl, 5 mM $MgCl_2$, pH 7.4) supplemented with 0.1% BSA, 0.1% bacitracin and 10 μM GDP. Membranes are incubated on ice for 20 minutes, transferred to a 96-well Millipore microtiter GF/C filter plate and mixed with GTPγ$^{35}$S (e.g., 250,000 cpm/sample, specific activity ~1000 Ci/mmol) plus or minus GTPγS (final concentration=100 μM). Final membrane protein concentration=90 μg/ml. Samples are incubated in the presence or absence of porcine galanin (final concentration=1 μM) for 30 min. at room temperature, then filtered on a Millipore vacuum manifold and washed three times with cold assay buffer. Samples collected in the filter plate are treated with scintillant and counted for $^{35}$S in a Trilux (Wallace) liquid scintillation counter. It is expected that optimal results are obtained when the mammalian receptor membrane preparation is derived from an appropriately engineered heterologous expression system, i.e., an expression system resulting in high levels of expression of the mammalian receptor described herein and/or expressing G-proteins having high turnover rates (for the exchange of GDP for GTP). GTPγS assays are well-known in the art, and it is expected that variations on the method described above, such as are described by e.g., Tian et al. (1994) or Lazareno and Eirdsall (1993), may be used by one of ordinary skill in the art.

MAP Kinase Assay

MAP kinase (mitogen activated kinase) may be monitored to evaluate receptor activation. MAP kinase is activated by multiple pathways in the cell. A primary mode of activation involves the ras/raf/MEK/MAP kinase pathway. Growth factor (tyrosine kinase) receptors feed into this pathway via SHC/Grb-2/SOS/ras. Gi coupled receptors are also known to activate ras and subsequently produce an activation of MAP kinase. Receptors that activate phospholipase C (Gq and G11) produce diacylglycerol (DAG) as a consequence of phosphatidyl inositol hydrolysis. DAG activates protein kinase C which in turn phosphorylates MAP kinase.

MAP kinase activation can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the mitogen and then extracted with Laemmli buffer. The soluble fraction is applied to an SDS-PAGE gel and proteins are transferred electrophoretically to nitrocellulose or Immobilon. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the mitogen and a soluble extract is prepared. The extract is incubated at 30° C., for 10 min with gamma-32-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatography paper is washed and counted for $^{32}$p in a liquid scintillation counter. Alternatively, the cell extract is incubated with gamma-32-ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then by aspirated through the filter, which retains the phosphorylated myelin basic protein. The filter is washed and counted for $^{32}$p by liquid scintillation counting.

Cell Proliferation Assay

Receptor activation of a G protein coupled receptor may lead to a mitogenic or proliferative response which can be monitored via $^{3}$H-thymidine uptake. When cultured cells are incubated with $^{3}$H-thymidine, the thymidine translocates into the nuclei where it is phosphorylated to thymidine triphosphate. The nucleotide triphosphate is then incorporated into the cellular DNA at a rate that is proportional to the rate of cell growth. Typically, cells are grown in culture for 1–3 days. Cells are forced into quiescence by the removal of serum for 24 hrs. A mitogenic agent is then added to the media. 24 hrs later, the cells are incubated with $^{3}$H-thymidine at specific activities ranging from 1 to 10 uCi/ml for 2–6 hrs. Harvesting procedures may involve trypsinization and trapping of cells by filtration over GF/C filters with or without a prior incubation in TCA to extract soluble thymidine. The filters are processed with scintillant and counted for $^{3}$H by liquid scintillation counting. Alternatively, adherent cells are fixed in MeOH or TCA, washed in water, and solubilized in 0.05% deoxycholate/0.1 N NaOH. The soluble extract is transferred to scintillation vials and counted for $^{3}$H by liquid scintillation counting.

It is to be understood that the cell lines described herein are merely illustrative of the methods used to evaluate the binding and function of the mammalian receptors of the present invention, and that other suitable cells may be used in the assays described herein.

Methods for Recording Currents in Xenopus Oocytes

Female *Xenopus laevis* (Xenopus-1, Ann Arbor, Mich.) are anesthetized in 0.2% tricain (3-aminobenzoic acid ethyl ester, Sigma Chemical Corp.) and a portion of ovary is removed using aseptic technique (Quick and Lester, 1994). Oocytes are defolliculated using 2 mg/ml collagenase (Worthington Biochemical Corp., Freehold, N.J.) in a solution containing 87.5 mM NaCl, 2 mM KCl, 2 mM $MgCl_2$ and 5 mM HEPES, pH 7.5. Oocytes may be injected (Nanoject, Drummond Scientific, Broomall, Pa.) with mammalian mRNA described in this invention. Other oocytes may be injected with a mixture of mammalian mRNA and mRNA encoding the genes for G-protein-activated inward rectifiers (GIRK1 and GIRK4). Genes encoding G-protein inwardly rectifying $K^+$ (GIRK) channels 1 and 4 (GIRK1 and GIRK4) were obtained by PCR using the published sequences (Kubo et al., 1993; Dascal et al., 1993; Krapivinsky et al., 1995 and 1995b) to derive appropriate 5' and 3' primers. Human heart cDNA was used as template together with the primers (Seq. I.D. No. 11)
5'-CGCGGATCCATTATGTCTGCACTCCGAAGGAAATTTG-3' and (Seq. I.D. No. 12)
5'-CGCGAATTCTTATGTGAAGCGATCAGAGTTCATTTTTC-3' for GIRK1 and (Seq. I.D. No. 13)
5'-GCGGGATCCGCTATGGCTGGTGATTCTAGGAATG-3' and (Seq. I.D. No. 14)
5'-CCGGAATTCCCCTCACACCGAGCCCCTGG-3' for GIRK4.

In each primer pair, the upstream primer contained a BamHI site and the downstream primer contained an EcoRI site to facilitate cloning of the PCR product into pcDNA1-Amp (Invitrogen). The transcription template for the mammalian receptor may be similarly obtained. mRNAs are prepared from separate DNA plasmids containing the complete coding regions of the mammalian receptor, GIRK1, and GIRK4. Plasmids are linearized and transcribed using the T7 polymerase ("Message Machine", Ambion). Alternatively, mRNA may be translated from a template generated by PCR, incorporating a T7 promoter and a poly $A^+$ tail. Each oocyte receives 2 ng each of GIRK1 and GIRK4 mRNA in combination with 25 ng of mammalian receptor mRNA. After injection of mRNA, oocytes are incubated at 16° on a rotating platform for 3–8 days. Dual electrode voltage clamp ("GeneClamp", Axon Instruments Inc., Foster City, Calif.) is performed using 3 M KCl-filled glass microelectrodes having resistances of 1–3 Mohms. Unless otherwise specified, oocytes are voltage clamped at a holding potential of −80 mV. During recordings, oocytes are bathed in continuously flowing (2–5 ml/min) medium containing 96 mM NaCl, 2 mM KCl, 2 mM $CaCl_2$, 2 mM $MgCl_2$, and 5 mM HEPES, pH 7.5 ("ND96"), or, in the case of oocytes expressing GIRK1 and GIRK4, elevated $K^+$ containing 96 mM KCl, 2 mM NaCl, 2 mM $CaCl_2$, 2 mM $MgCl_2$, and 5 mM HEPES, pH 7.5 ("hK"). Drugs are applied by switching from a series of gravity fed perfusion lines.

Heterologous expression of GPCRs in Xenopus oocytes has been widely used to determine the identity of signaling pathways activated by agonist stimulation (Gundersen et al., 1983; Takahashi et al., 1987). Activation of the phospholipase C (PLC) pathway is assayed by applying test compound in ND96 solution to oocytes previously injected with mRNA for the mammalian receptor and observing inward currents at a holding potential of −80 mV. The appearance of currents that reverse at −25 mV and display other properties of the $Ca^{++}$-activated $Cl^-$ (chloride) channel is indicative of mammalian receptor-activation of PLC and release of IP3 and intracellular $Ca^{++}$. Such activity is exhibited by GPCRs that couple to $G_q$.

Measurement of inwardly rectifying $K^+$ (potassium) channel (GIRK) activity is monitored in oocytes that have been co-injected with mRNAs encoding the mammalian receptor, GIRK1, and GIRK4. The two GIRK gene products co-assemble to form a G-protein activated potassium channel known to be activated (i.e., stimulated) by a number of GPCRs that couple to $G_i$ or $G_o$ (Kubo et al., 1993; Dascal et al., 1993). Oocytes expressing the mammalian receptor plus the two GIRK subunits are tested for test compound responsivity by measuring $K^+$ currents in elevated K solution (hK). Activation of inwardly rectifying currents that are sensitive to 300 $\mu$M $Ba^{++}$ signifies the mammalian receptor coupling to a $G_i$ or $G_o$ pathway in the oocytes.

In vivo Methods

The effects of administration of human Ob-Re receptor protein and related receptors may be evaluated by intravenous (i.v.) injection of the receptor followed by measurement of food intake in the animal. Measurement of food intake may be performed for 3 hours after injection, but other protocols may also be used. Saline may be injected as a control, but it is understood that other vehicles may be required as controls for some peptides and compounds.

Materials

Cell culture media and supplements are from Specialty Media (Lavallette, N.J.). Cell culture plates (150 mm and 96-well microtiter) are from Corning (Corning, N.Y.). Sf9, Sf21, and High Five insect cells, as well as the baculovirus transfer plasmid, pBlueBacIII™, are purchased from Invitrogen (San Diego, Calif.). TMN-FH insect medium complemented with 10% fetal calf serum, and the baculovirus DNA, BaculoGold™, is obtained from Pharmingen (San Diego, Calif.). Ex-Cell 400™ medium with L-Glutamine is purchased from JRH Scientific. Polypropylene 96-well microtiter plates are from Co-star (Cambridge, Mass.). All radioligands are from New England Nuclear (Boston, Mass.).

Peptides were either from Bachem California (Torrance, Calif.), Peninsula (Belmont, Calif.); or were synthesized by custom order from Chiron Mimotopes Peptide Systems (San Diego, Calif.). Leptin and [$^{125}$I] leptin were provided by Novartis. (See also W096/05309.) Leptin and [$^{125}$I] leptin are also commercially available from BACHEM and NEN-Dupont, respectively. Bio-Rad Reagent was from Bio-Rad (Hercules, Calif.). Bovine serum albumin (ultra-fat free, A-7511) was from Sigma (St. Louis. Mo.). All other materials were reagent grade.

Experimental Results

3' RACE of Human RNAs for hOb-Re

The Ob-R gene consists of multiple exons which can give rise to several splice variants (Lee et al., 1996). The mOb-Re sequence is identical to the mOb-Ra,b,c and d receptors until nucleotide 2389 of the mOb-Rb receptor, and then diverges to encode 9 unique amino acids (Lee et al., 1996). The sequence of the mOb-Ra,b,c and d receptors are identical until nucleotide 2667 of mOb-Rb, at which point each has an alternative 3' end (Lee et al., 1996). FIG. 1 illustrates the likely genomic structure for the 3' end of the mouse Ob-R gene. While two exons in the 5' region common to all splice variants are illustrated, the actual number of these is not presently known. The human Ob-Rb and Ob-Ra receptors have been cloned and the hOb-R gene appears to have a similar structure to the mouse (Tartaglia et al, 1995; Cioffi et al., 1996). Assuming that the hOb-Re-specific sequence would be located in an analogous location as found in the mouse, we performed 3'RACE on human cDNAs in order to identify the human Ob-Re splice variant. 3' RACE was performed using several nested primer sets, as illustrated in Table 1. 3' RACE products were sequenced, identifying hOb-Ra and HuB219.1 in human kidney, heart, skeletal muscle, adipose and lung. hOb-Rb was also identified in kidney. However, 3' sequences homologous to mOb-Re were not identified in any of these tissues.

Low Stringency PCR for hOb-Re

The sequences for the mouse and human Ob-Ra share 82% nucleotide identity. We therefore attempted to use the mOb-Re-specific sequence to amplify the hOb-Re gene. Low stringency PCR was performed on human kidney, liver, skeletal muscle and heart using a forward primer from a common region of hOb-R (DC4) and a reverse primer from the mouse Ob-Re sequence (BB116). No bands were amplified in any of these tissues.

Identification of Human Ob-Re-Specific Sequence

Figure 2A:
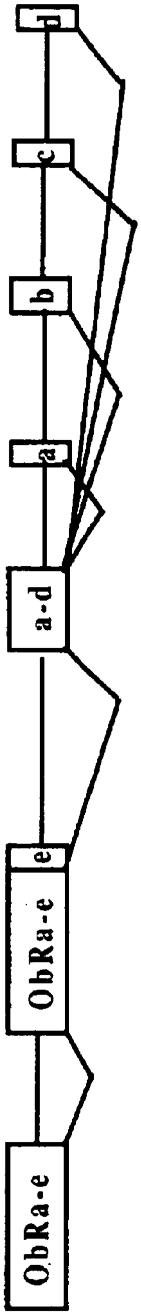
FIGS. 2*a* and 2*b* Schematic illustrating the two potential structures of the 3' end of the mouse Ob-R gene based on current findings. Boxes represent exons, horizontal lines represent introns, and diagonal lines indicate exon splicing.
Figure 2B:
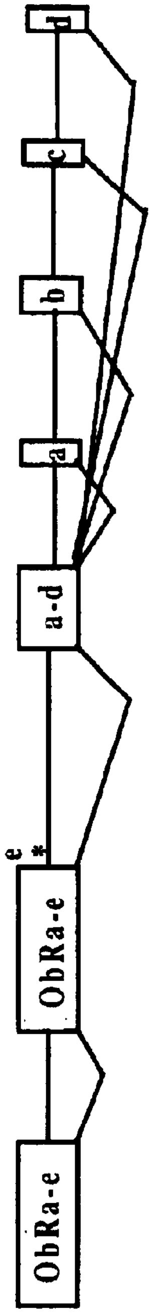
Figure 6A:
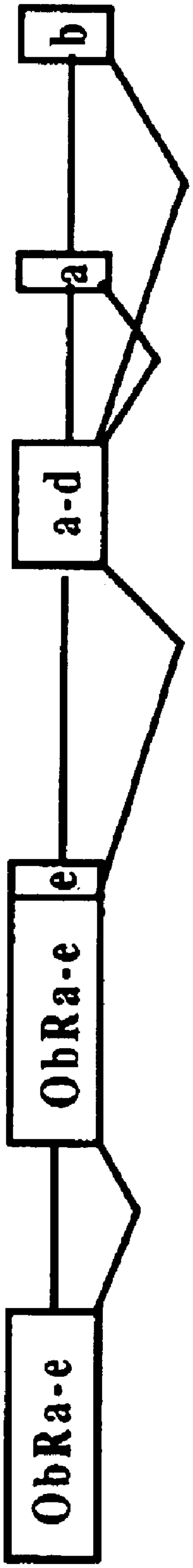
FIGS. 6*a* and 6*b* Schematics illustrating the two potential structures of the 3' end of the human Ob-R gene based on current findings. Boxes represent exons, horizontal lines represent introns, and diagonal lines indicate exon splicing.
Figure 6B:
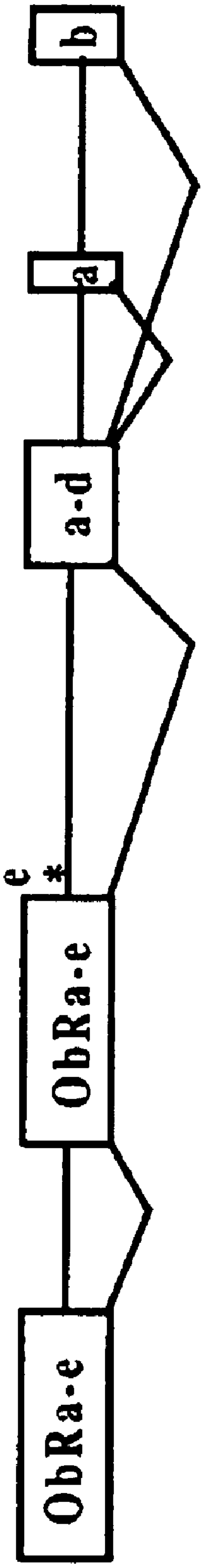
Figure 7A:
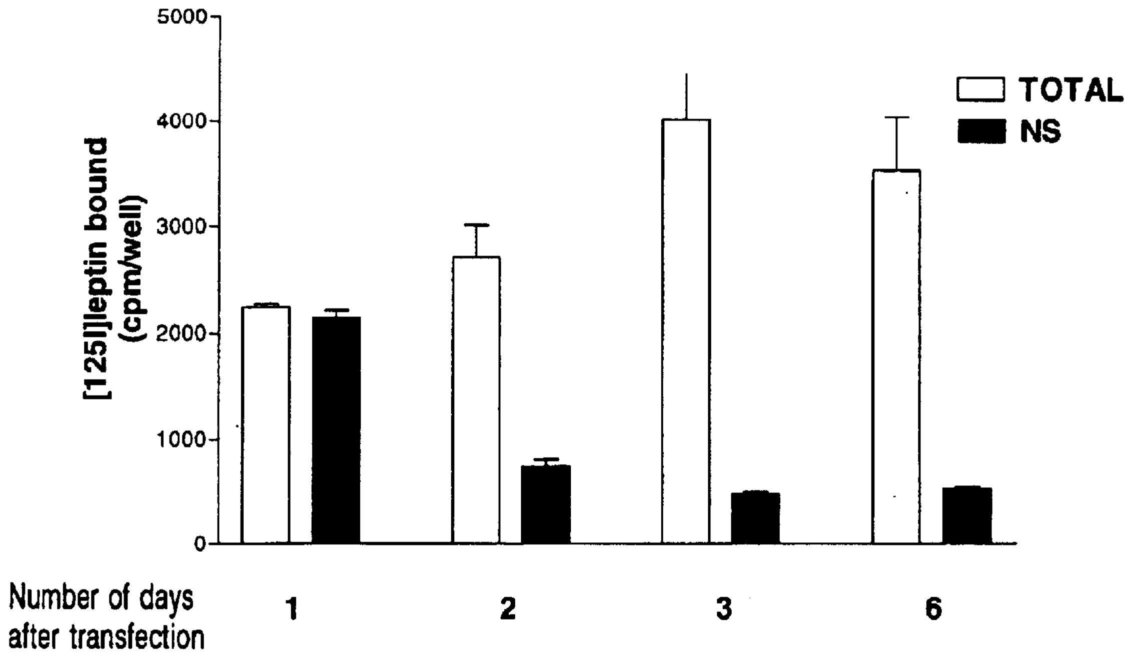
FIGS. 7*a*–7*d* optimization of binding of [$^{125}$I] leptin to Mock—(vector only) and hOb-Re-transfected Cos-7 cells. Cos-7 cells were transiently transfected as described under Methods. Following transfection, cells were incubated for the indicated number of days and binding of [$^{125}$I] leptin was measured in the medium (FIG. 7*a*) as well as on the cells (FIG. 7*c*) using SPA beads (see Methods). Binding of [$^{125}$I] leptin in medium (FIG. 7*b*) or on cells (FIG. 7*d*) was determined in the manner using mock (vector only) transfected cells. Results are expressed as cpm bound/well. Experiments were carried out in triplicate.
Figure 7B:
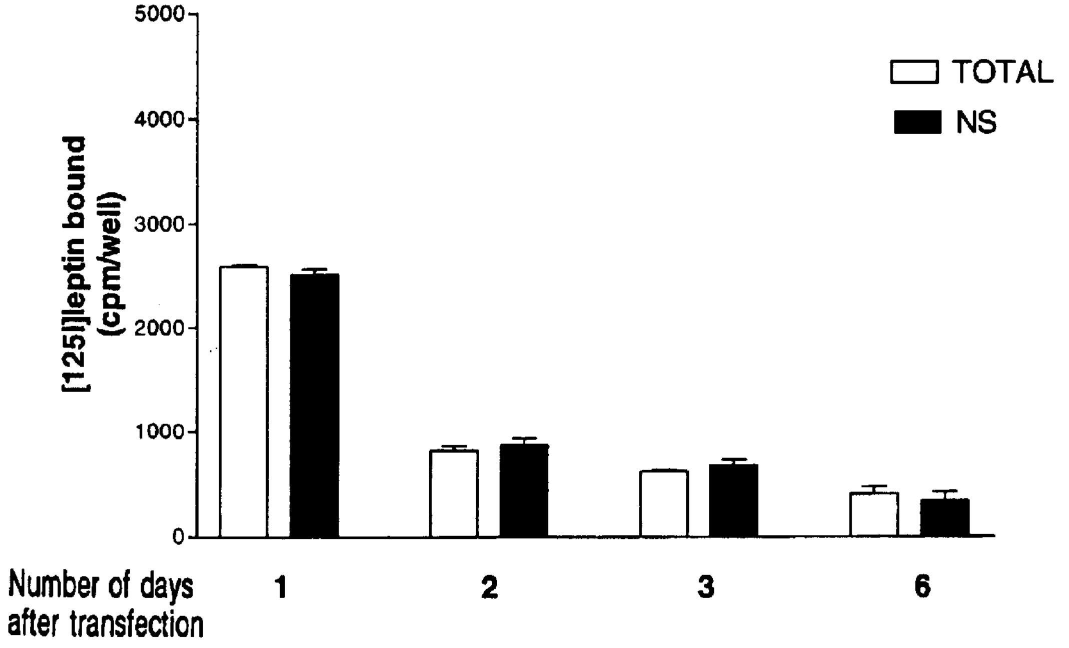
Figure 7C:
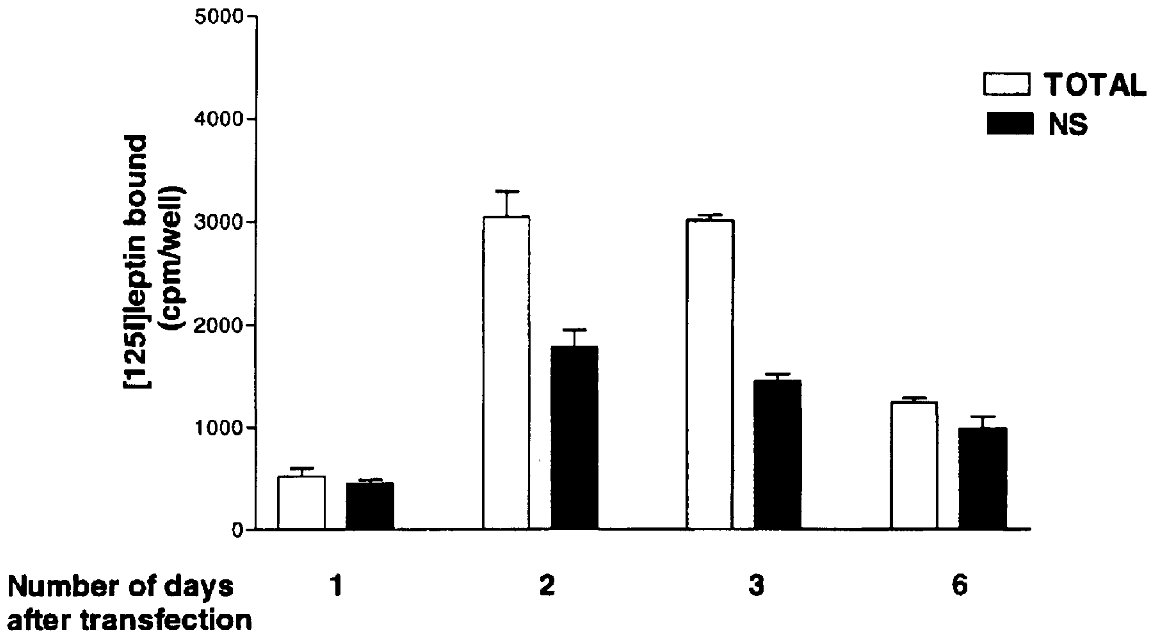
Figure 7D:
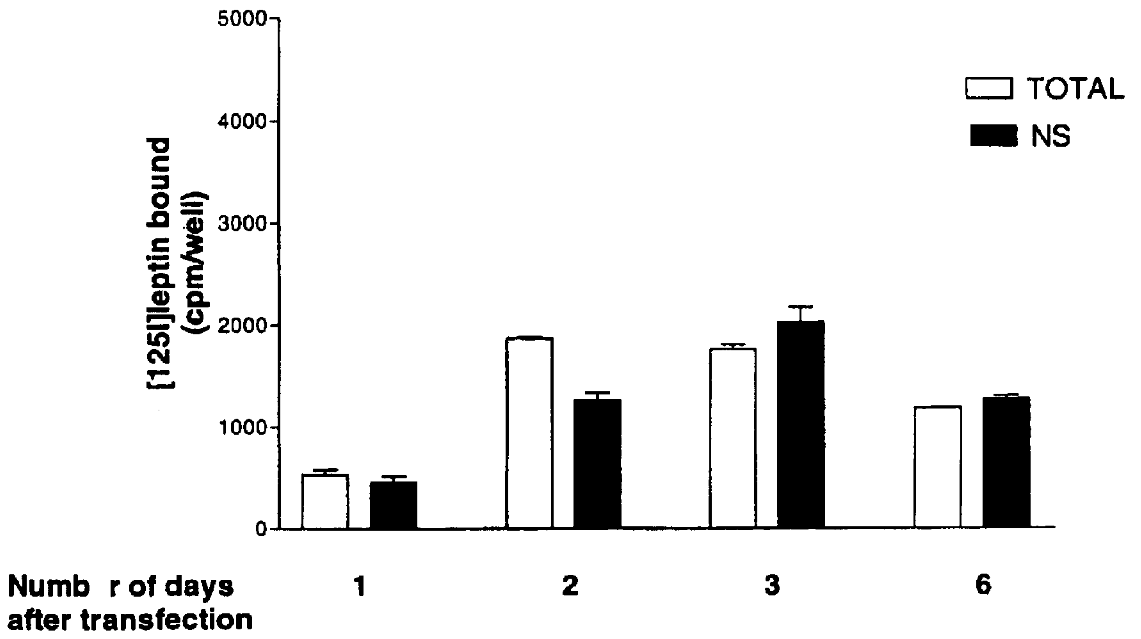

FIG. 1 illustrates the likely genomic structure of the 3' end of the mOb-R gene based on previous findings (Lee et al., 1996). To identify the location of the mOb-Re-specific exon, we amplified mouse genomic DNA using PCR primers from the exons believed to be immediately upstream (BB130) and downstream (BB131) of the mOb-Re-specific exon (FIG. 1). Upon sequencing this portion of genomic DNA, it was revealed that the mOb-Re-specific sequence is located immediately downstream of the upstream common exon, with no intervening intron. This new finding suggests that the genomic structure of the mOb-R gene actually contains either two contiguous exons (FIG. 2*a*) or that the Ob-Re-specific sequence is encoded by an unspliced intron (FIG. 2*b*) We next performed a similar experiment on human genomic DNA in order to determine if the hOb-Re-specific sequence is encoded in a similar manner, and to identify the hOb-Re sequence. Human genomic DNA was amplified using PCR primers from the hOb-R exons immediately upstream (DC4) and downstream (BB132) of the analogous exons that flank the mOb-Re-specific sequence. A 2.2 kb product was sequenced and found to be identical to hOb-Rb from DC4 up to nucleotide 2495, after which it diverged completely from any of the published hOb receptors. This novel sequence contained an open reading frame encoding 6 amino acids, and shares 83% nucleotide identity to the mouse Ob-Re-specific sequence (FIG. 3). The nucleotide sequence of the complete coding region of human Ob-Re is shown in FIG. 4. The deduced amino acid sequence is shown in FIG. 5. These new findings suggest that the hOb-R gene contains either two contiguous exons (FIG. 6*a*) or that the hOb-Re-specific sequence is encoded by an unspliced intron (FIG. 6*b*).

Localization of Ob-Re in Human Tissues hOb-Re was originally identified in human genomic DNA. In order to determine if this receptor isoform is expressed in tissues, we performed RT-PCR to identify human tissues that express hOb-Re. hOb-Re was not detected by PCR in cDNA prepared from human hypothalamus, total brain, heart, kidney, skeletal muscle, liver, lung or adipose. To increase the level of detection, we repeated the PCR using as a template products from 3' RACE reactions. However, hOb-Re was not detected by PCR using as a template first PCR products of 3' RACE reactions from human heart, skeletal muscle and adipose. hOb-Re was amplified from the first PCR of a 3' RACE reaction from lung. Using a forward PCR primer corresponding to a region of Ob-Rb two exons upstream from the Ob-Re-specific sequence (BB16), and nested reverse primers from within the hOb-Re-specific sequence (BB138 and BB139), a 2 kb and a 0.26 kb band were amplified from human lung cDNA while only a 2 kb band was amplified from human genomic DNA. DNA sequencing revealed that the 2 kb band contained an intron while the 0.26 kb band contained the sequence for the 3' end of the hOb-Re receptor. This demonstrates that although there was some genomic contamination in the human lung cDNA, this cDNA also expresses the processed Ob-Re message.

Expression of hOb-Re in COS-7 Cells

Figure 8:
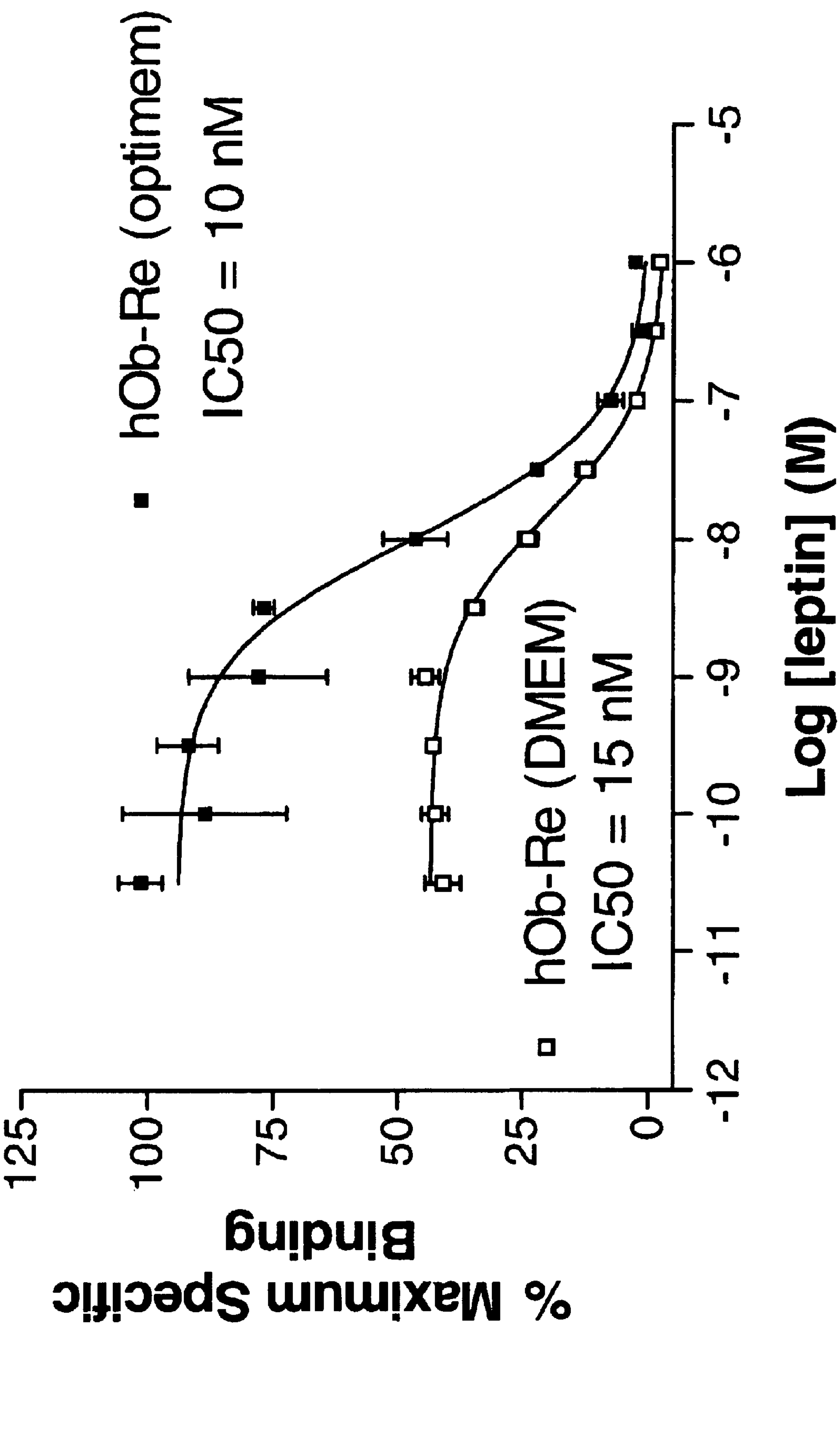
FIG. 8 Effect of different growth media on the binding of [$^{125}$I] leptin to hOb-Re receptor. Cos-7 cells were transfected with hOb-Re as described in the Methods and grown in either optimem or DMEM medium. Binding of [$^{25}$I] leptin was evaluated 48 hrs following transfection, using SPA beads as described in the Methods. Results are expressed as % maximum specific binding obtained in the absence of unlabeled leptin. Experiments were carried out in triplicate and results are means±S.E.M. $IC_{50}$ values indicate the concentration or unlabeled leptin displacing 50% of maximum specific binding. Binding data were analyzed by nonlinear regression analysis.
Figure 9:
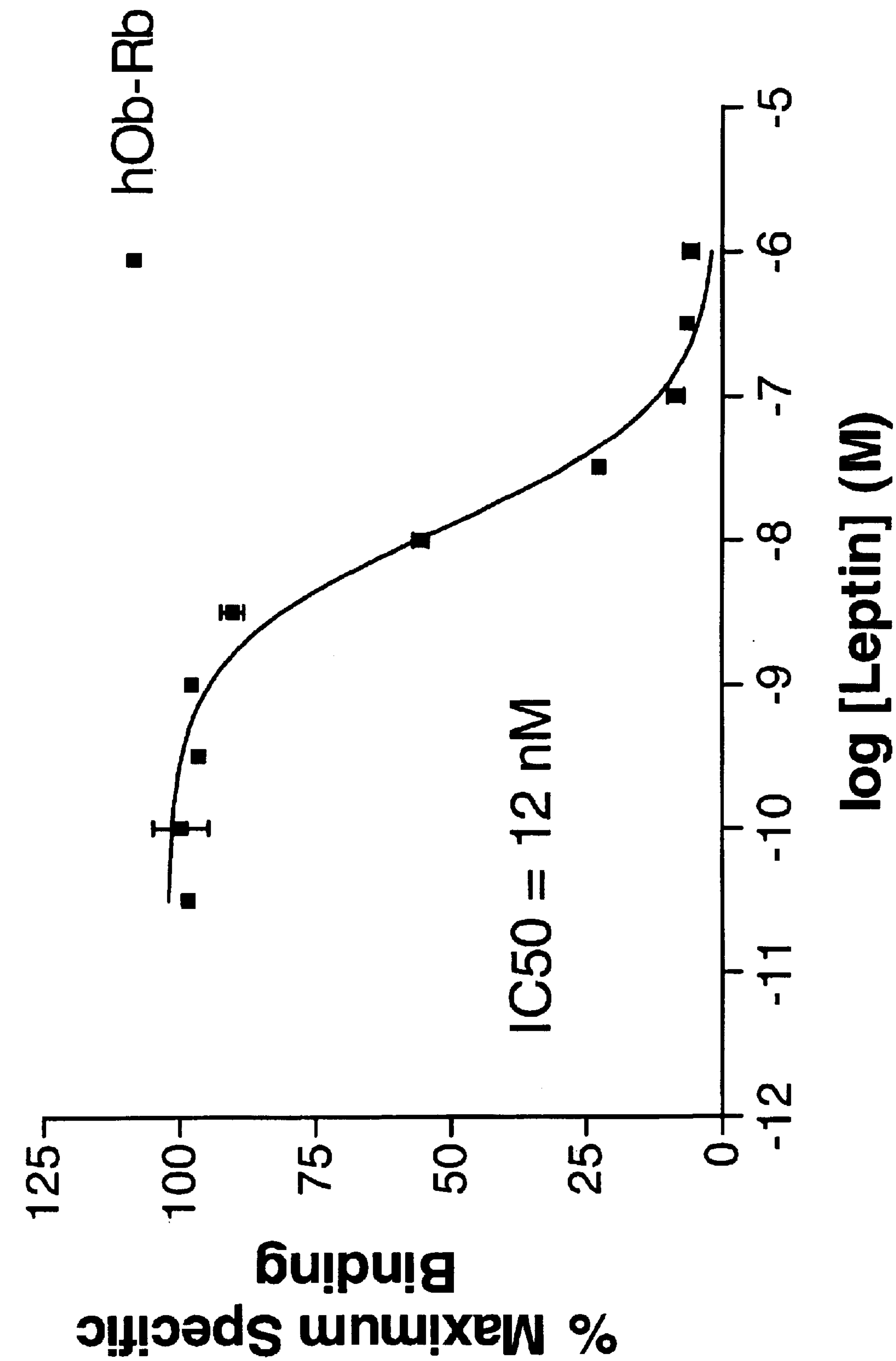
FIG. 9 Displacement of [$^{125}$I] leptin binding by unlabeled leptin on Cos-7 cells transfected with human Ob-Rb. Cos-7 cells were transfected with human Ob-Rb as described in the Methods. Binding of [$^{125}$I] leptin was evaluated 48 hours following transfection using SPA beads as described in the Methods. Results are expressed as % maximum specific binding obtained in the absence of unlabeled leptin. Experiments were carried out in triplicate and results are means±S.E.M. $IC_{50}$ values indicate the concentration of unlabeled leptin displacing 50% of maximum specific binding. Binding data were analyzed by nonlinear regression analysis.
Figure 10A:
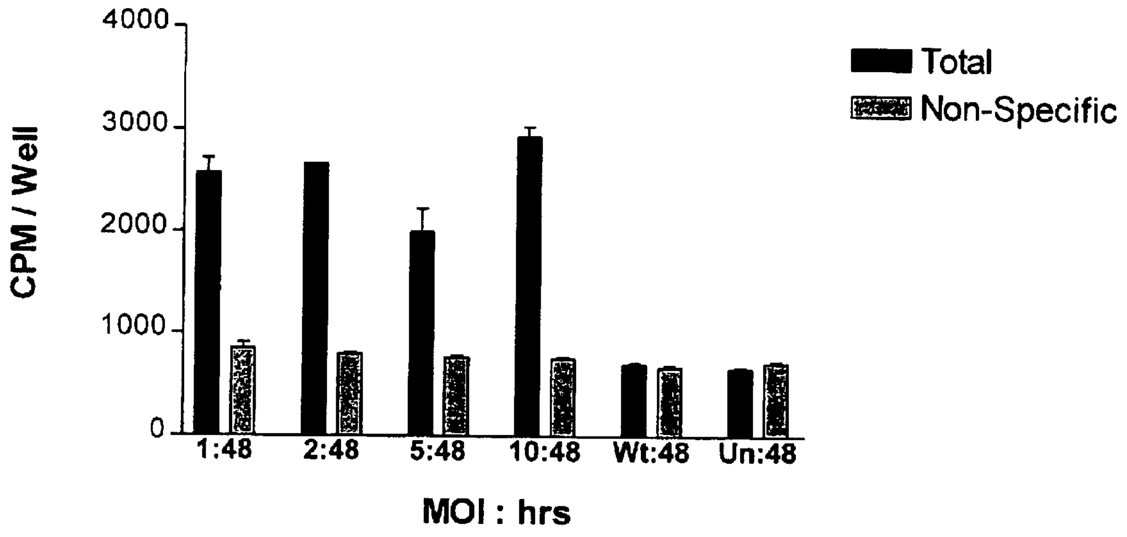
FIGS. 10*a*–10*d* Optimization of binding of [$^{125}$I] leptin to hOb-Re from transfected SF21 insect cells. hOb-Re was expressed in SF21 insect cells and binding assays were conducted to optimize both the MOI and the time course for binding as described in Methods. MOI of 1–10 and supernatant collected after 48 hours (FIG. 10*a*), 72 hours.
Figure 10B:
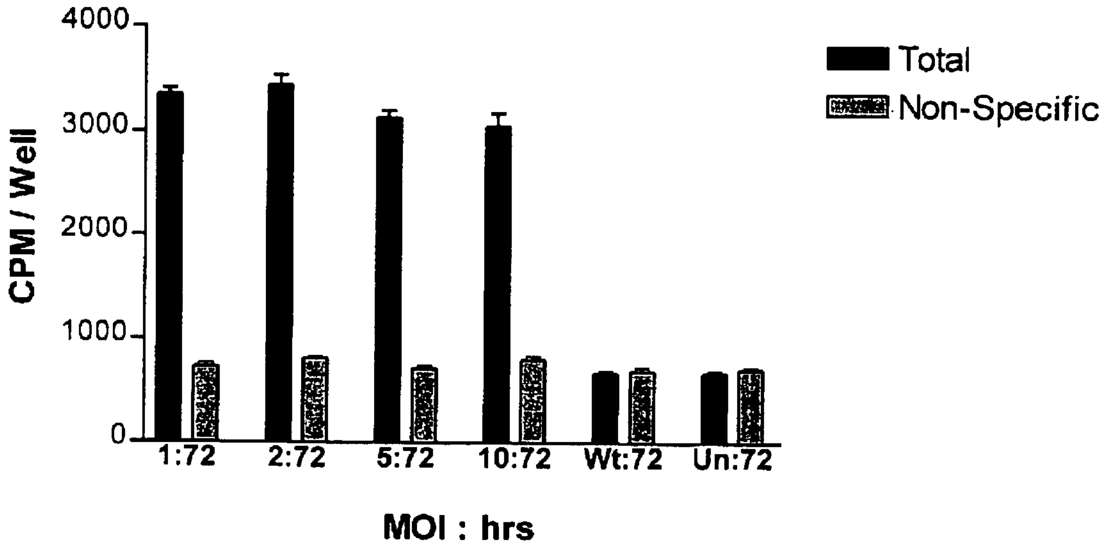
Figure 10C:
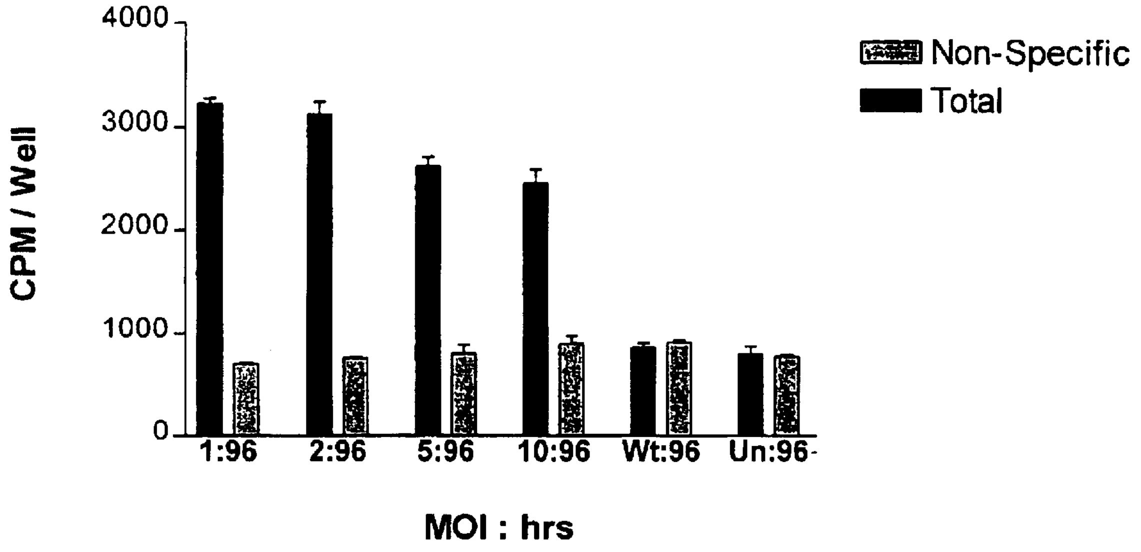
Figure 10D:
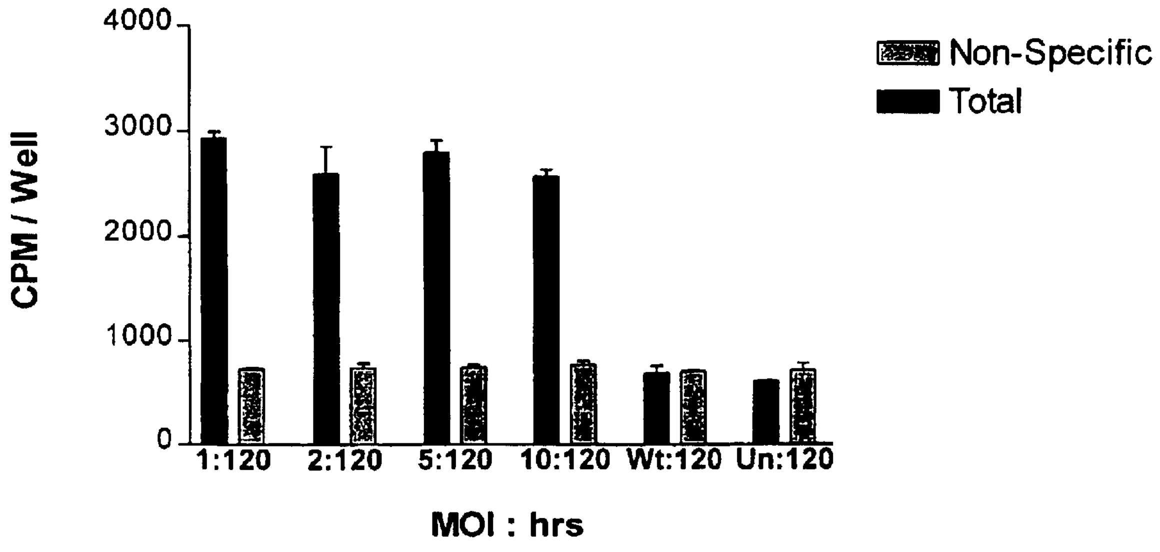

We tested [$^{125}$I] leptin binding using SPA on both the medium and the cells of hOb-Re-transfected COS-7 cells over 1–6 days post-transfection. Binding signal was significantly better for the medium although some level of specific binding was observed on cells also (FIG. 7). No binding signal was observed either in the medium or the cells of mock-transfected plates. Binding signal was optimum between 2–3 days post-transfection (FIG. 8). The maximum specific binding was 2-fold greater in optimem medium vs. normal DMEM medium. The $IC_{50}$ value obtained for unlabeled leptin displacement of [125I ] leptin for hOb-Re was comparable to that obtained for hOb-Rb using SPA ($IC_{50}$ 10–15 nM; FIG. 9).

Expression of hOb-Re in Insect Cells

Figure 11A:
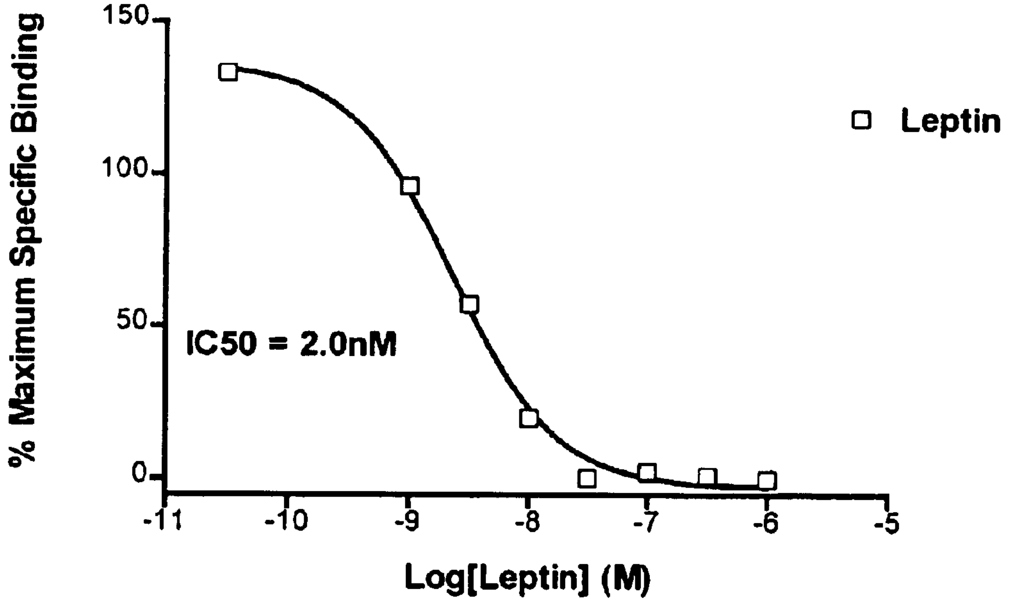
FIGS. 11*a* and 11*b* Affinity of unlabeled leptin for hOb-Re receptor from infected insect SF21 cells. The cells were infected with BO45 viral stock either undiluted (FIG. 11*a*) or diluted 1:2 (FIG. 11*b*). 500 mL of a high titer stock of virus was prepared at an MOI of 0.1 and supernatant was collected 5 days post infection and tested for binding, as described in the Methods. Results are expressed as % maximum specific binding obtained in the absence of unlabeled leptin. Experiments were carried out in triplicate. $IC_{50}$ values indicate the concentration of unlabeled leptin displacing 50% of maximum specific binding. Binding data were analyzed by nonlinear regression analysis.
Figure 11B:
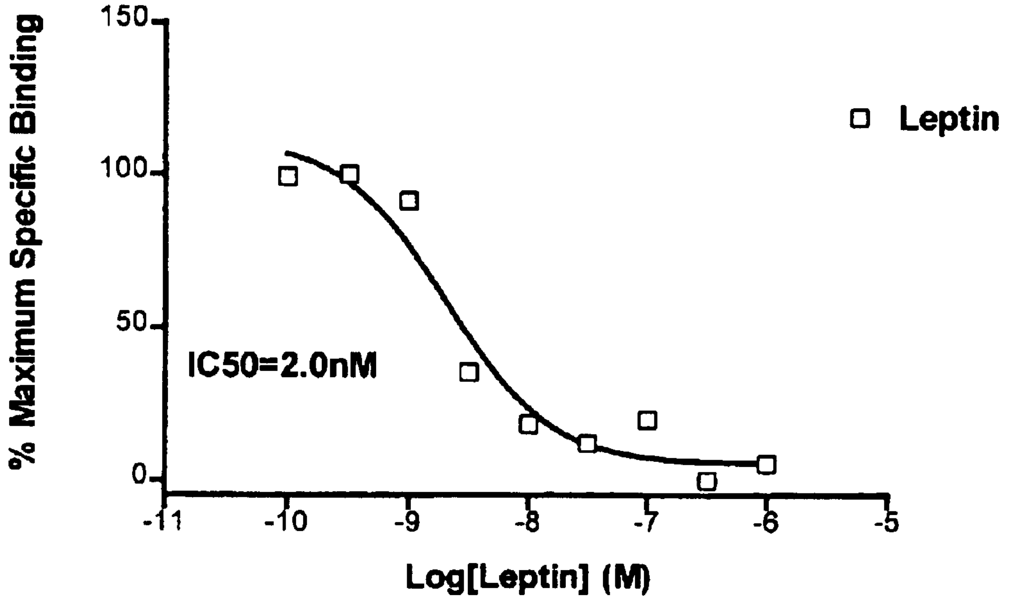

A baculovirus expression system was used to express hOb-Re in SF21 insect cells. Assays were conducted to optimize both the MOI and the time course for binding. An MOI of 1–10 and supernatant collected between 2–5 day post-infection were evaluated (FIG. 10). There were no significant differences in binding between the different MOI concentrations. Binding appeared somewhat better 3 days post-infection compared to other time points. Finally, 500 mL of a high titer stock of virus was prepared at an MOI of 0.1 and supernatant was collected 5 days post infection. This viral stock may be used to infect insect cells on a large scale for mass production of hOb-Re protein. A sample of this high titer stock was tested for binding. Unlabeled leptin displaced [$^{125}$I] leptin binding to hOb-Re receptor expressed by insect cells with a high affinity ($IC_{50}$ about 2 nM; FIG. 11).

TABLE 1

Primer sets used in 3' RACE experiments

| Human Tissue | First PCR Primer Set | Nested PCR Primer Set |
|---|---|---|
| Kidney | AP1 BB75 | AP2 BB76 |
| | AP1 BB76 | AP2 DC4 |
| | AP1 BB76 | AP2 BB87 |
| | AP1 DC17 | AP2 DC18 |
| Liver | AP1 DC17 | AP2 DC18 |
| | AP1 DC17 | AP2 DC4 |
| Skeletal Muscle | AP1 DC17 | AP2 DC18 |
| | AP1 DC17 | AP2 DC4 |
| Heart | AP1 BB75 | AP2 DC4 |
| | AP1 BB76 | AP2 DC4 |
| | AP1 DC17 | AP2 DC18 |
| | AP1 DC17 | AP2 DC4 |
| adipose | AP1 DC17 | AP2 DC18 |
| Lung | AP1 DC17 | AP2 DC18 |

TABLE 2

| Primers used: | |
|---|---|
| BB75 (nucs 919–944 of hOb-Rb):<br>5' CAGGTGAGGGGCAAGAGACTGGATGG 3'. | (Seq. I.D. No. 15) |
| BB76 (nucs 2122–2148 of hOb-Rb):<br>5' CAAGCACATACTGTTACGGTTCTGGCA 3'. | (Seq. I.D. No. 16) |
| BB87 (nucs 2632–2657 of hOb-Rb):<br>5' CCCAAGAATTGTTCCTGGGCACAAGG 3'. | (Seq. I.D. No. 17) |
| BB116 (nucs 2413–2390 of mOb-Re and nucs 2394–2391 of hOb-Rb:<br>5' CCATGAAAAGTACAGTACACATACCATGG 3'. | (Seq. I.D. No. 18) |
| BB130 (nucs 2238–2262 of mOb-Rb):<br>5' CCTGAGCAGCAGCTGTGTCATCCTT 3'. | (Seq. I.D. No. 19) |
| BB131 (nucs 2513–2488 of mOb-Rb):<br>5' GCGTCATTCTGCTGCTTGTCGATAGC 3'. | (Seq. I.D. No. 20) |

TABLE 2-continued

| Primers used: | |
|---|---|
| BB132 (nucs 2438–2413 of hOb-Rb):<br>5' GGGTAAAGACTGAACTGGTACTTCTC 3'. | (Seq. I.D. No. 21) |
| BB138 (nucs 2391–2415 of hOb-Re):<br>5' CTAAAGTATAGTAAACTTACCATGG 3'. | (Seq. I.D. No. 22) |
| BB139 (from 3'UT of hOb-Re):<br>5' GGATTATATGTATTAGGATGGTAGTATCC 3'. | (Seq. I.D. No. 23) |
| BB157 (from nucs 2372-2395 of hOb-Rb and nucs 2396-2415 of hOb-Re:<br>5' TCTGTTAAGAAGTATTATATCCATGGTAAGTTTACTATACTTTAGTAATGAATGA 3'. | (Seq. I.D. No. 24) |
| BB158 (from nucs 2415-2396 of hOb-Re of hOb-Rb and nucs 2395-2372:<br>5' AGCTTCATTCATTACTAAAGTATAGTAAACTTACCATGGATATAATACTTCTTAAC 3'. | (Seq. I.D. No. 25) |
| DC4 (nucs 2218-2243 of hOb-Rb):<br>5' ATCGTGCAGTCACTCAGTGCTTATCC 3'. | (Seq. I.D. No. 26) |
| DC16 (nucs 2145-2174 of hOb-Rb):<br>5' GGCCATCAATTCAATTGGTGCTTCTGTTGC 3'. | (Seq. I.D. No. 27) |
| DC17 (nucs 1874-1902 of hOb-Rb):<br>5' GGAGCAATCCAGCCTACACAGTTGTCATG 3'. | (Seq. I.D. No. 28) |
| DC18 (nucs 2057-2085 of hOb-Rb):<br>5' CCTGCAATGGAACATGGTCAGAAGATG 3'. | (Seq. I.D. No. 29) |

References

Burns, C. M., Chu, H., Rueter, S. M., Sanders-Bush, E., and R. B. Erneson. (1996) Neuroscience Abstracts 385.9.

Cheng, Y. C. and Prusoff, W. H. (1973). Relationship between the inhibition constant (Ki) and the concentration of inhibitor which causes 50% inhibition ($IC_{50}$) of an enzyme reaction. *Biochem. Pharmacol.* 22:3099–3108.

Chu, H., Burns, C., Canton, H., Emeson, R. B., and E. Sanders-Bush. (1996) Neuroscience Abstracts 385.10.

Cullen, B. (1987) Use of eukaryotic expression technology in the functional analysis of cloned genes. *Meth. Enzymol.* 152:685–704.

Cioffi, J. A., Shafer, A. W., Zupanic, T. J., Smithe-Gbur, J., Mikhail, A., Platika, D., and Snodgrass, H. R. (1996). Novel B219/OB receptor isoforms: Possible role of leptin in hematopoiesis and reproduction. *Nature Medicine* 2:585–589.

Dascal, N., Schreibmayer, W., Lim, N. F., Wang, W., Chavkin, C., DiMagno, L., Labarca, C., Kieffer, B. L., Gaveriaux-Ruff, C., Trollinger, D., Lester, H. A., Davidson, N. (1993) Proc. Natl. Acad. Sci. USA 90:10235–10239.

Gundersen, C. B., Miledi, R., Parker, I. (1983) Proc. R. Soc. London Ser. B 219:103–109.

Krapivinsky, G., Gordon, E. A., Wickman, B., Velimirovic, B., Krapivinsky, L., Clapham, D. E. (1995) Nature 374:135–141.

Kubo, Y., Reuveny, E., Slesinger, P. A., Jan, Y. N. and Jan, L. Y. (1993) Nature 364:802–806.

Lazareno, S. and Birdsall, N. (1993) Br. J. Pharmacol. 109:1120–1127.

Lee, G.-H., Proenca, R., Montez, J. M., Carroll, K. M., Dirvishzadeh, J. G, Lee, J. I, and Friedman, J. M. (1996). Abnormal splicing of the leptin receptor in diabetic mice. *Nature* 379:632–635.

Quick, M. W. and Lester, H. A. (1994) Meth. Neurosci. 19:261–279.

Takahashi, T., Neher, E., and Sakmann, B. (1987) Proc. Natl. Acad. Sci. USA 84:5063–6067.

Tartaglia, L. A., Dembski, M., Weng, X., Deng, N., Culpepper, J., Devos, R., Richards, G. J., Campfield, L. A., Clark, F. T., Deeds, J., Muir, C, Sanker, S., Moriarty, A., Moore, K. J., Smutko, J. S., Mays, G. G., Woolf, E. A., Monroe, C. A., and Tepper, R. I. (1995). Identification and expression cloning of a leptin receptor, OB-R. *Cell* 83:1263–1271.

Tian, W. N., Duzic, E., Lanier, S., and Deth, R. C. (1994) Mol. Pharmacol. 45:524–531.

What is claimed is:

1. A process for determining whether a chemical compound specifically binds to:

(a) a soluble polypeptide comprising consecutive amino acids, the amino acid sequence of which is shown in FIG. 5 (SEQ ID NO: 10); or (b) a soluble polypeptide having a sequence which varies therefrom by no more than 15 amino acids, such variations:

(i) not involving amino acids corresponding to the amino acids at positions 799–804 of the amino acid sequence shown in FIG. 5 (SEQ ID NO: 10); and (ii) not changing the functional properties of the soluble polypeptide; or (c) a soluble polypeptide comprising the soluble polypeptide of (a) or (b) linked to the following consecutive amino acids: Asp Tyr Lys Asp Asp Asp Asp Lys, which comprises contacting the soluble polypeptide of (a), (b) or (c) above with the compound under conditions suitable for binding, and detecting specific binding of the chemical compound to the soluble polypeptide.

2. The process of claim 1, wherein the specific binding of the compound to the polypeptide is detected by a scintillation proximity assay.

3. The process of claim 1, wherein the soluble polypeptide comprises consecutive amino acids, the amino acid sequence of which is shown in FIG. 5 (SEQ ID NO: 10).

4. A process involving competitive binding for determining whether a first chemical compound specifically binds to:

(a) a soluble polypeptide comprising consecutive amino acids, the amino acid sequence of which is shown in FIG. 5 (SEQ ID NO: 10); or (b) a soluble polypeptide having a sequence which varies therefrom by no more than 15 amino acids, such variations:

(i) not involving amino acids corresponding to the amino acids at positions 799–804 of the amino acid sequence shown in FIG. 5 (SEQ ID NO: 10); and (ii) not changing the functional properties of the soluble polypeptide; or (c) a soluble polypeptide comprising the soluble polypeptide of (a) or (b) linked to the following consecutive amino acids: Asp Tyr Lys Asp Asp Asp Asp Lys, which comprises separately contacting the soluble polypeptide of (a), (b) or (c) above, with both the first chemical compound and a second chemical compound known to bind to the soluble polypeptide, and separately with only the second chemical compound, under conditions suitable for binding of both the first and second compounds, and detecting specific binding of the first chemical compound to the soluble polypeptide, a decrease in the binding of the second chemical compound to the soluble polypeptide in the presence of the first chemical compound indicating that the first chemical compound binds to the soluble polypeptide.

5. The process of claim 4, wherein the specific binding of the compound to the polypeptide is detected by a scintillation proximity assay.

6. The process of claim 4, wherein the soluble polypeptide comprises consecutive amino acids, the amino acid sequence of which is shown in FIG. 5 (SEQ ID NO: 10).

7. A method of screening a plurality of chemical compounds not known to bind to:

(a) a soluble polypeptide comprising consecutive amino acids, the amino acid sequence of which is shown in FIG. 5 (SEQ ID NO: 10); or (b) a soluble polypeptide having a sequence which varies therefrom by no more than 15 amino acids, such variations:

(i) not involving amino acids corresponding to the amino acids at positions 799–804 of the amino acid sequence shown in FIG. 5 (SEQ ID NO: 10); and (ii) not changing the functional properties of the soluble polypeptide; or (c) a soluble polypeptide comprising the soluble polypeptide of (a) or (b) linked to the following consecutive amino acids: Asp Tyr Lys Asp Asp Asp Asp Lys, to determine whether a compound specifically binds to the soluble polypeptide of (a), (b) or (c) which comprises:

(1) preparing a cell extract or cell supernatant from cells transfected with and expressing DNA encoding the soluble polypeptide and contacting the cell extract or cell supernatant with a compound known to bind specifically to the soluble polypeptide;

(2) contacting the preparation of step (1) with the plurality of compounds not known to bind specifically to the soluble polypeptide, under conditions permitting binding of compounds known to bind the soluble polypeptide;

(3) determining whether the binding of the compound known to bind to the soluble polypeptide is reduced in the presence of the compounds, relative to the binding of the compound in the absence of the plurality of compounds; and if so (4) separately determining the binding to the soluble polypeptide of each compound included in the plurality of compounds, so as to thereby determine whether a compound specifically binds to the soluble polypeptide of (a), (b) or (c).

8. The method of claim 7, wherein the cell is a mammalian cell.

9. The method of claim 8, wherein the mammalian cell is non-neuronal in origin.

10. The method of claim 9, wherein the non-neuronal cell is a COS-7 cell, a 293 human embryonic kidney cell, an LM(tk−) cell or an NIH-3T3 cell.

11. A process of obtaining a composition which comprises:

(a) obtaining a chemical compound;

(b) determining whether the chemical compound binds to a soluble polypeptide by the process of any of claim 1, 2, 3, 4, 5 or 6 and (c) admixing a carrier and the chemical compound.

12. The method of claim 11, wherein the carrier is a pharmaceutically acceptable carrier.

* * * * *